United States Patent
Echigo et al.

(10) Patent No.: US 9,182,666 B2
(45) Date of Patent: Nov. 10, 2015

(54) CYCLIC COMPOUND, METHOD FOR PRODUCING THE SAME, RADIATION-SENSITIVE COMPOSITION, AND RESIST PATTERN FORMATION METHOD

(71) Applicant: MITSUBISHI GAS CHEMICAL COMPANY, INC., Tokyo (JP)

(72) Inventors: Masatoshi Echigo, Hiratsuka (JP); Masako Yamakawa, Hiratsuka (JP)

(73) Assignee: MITSUBISHI GAS CHEMICAL CO., INC., Tokyo (JP)

( * ) Notice: Subject to any disclaimer, the term of this patent is extended or adjusted under 35 U.S.C. 154(b) by 0 days.

(21) Appl. No.: 14/359,081

(22) PCT Filed: Nov. 14, 2012

(86) PCT No.: PCT/JP2012/079528
§ 371 (c)(1),
(2) Date: May 16, 2014

(87) PCT Pub. No.: WO2013/073582
PCT Pub. Date: May 23, 2013

(65) Prior Publication Data
US 2014/0329178 A1    Nov. 6, 2014

(30) Foreign Application Priority Data
Nov. 18, 2011   (JP) .................. 2011-253312

(51) Int. Cl.
| | |
|---|---|
| C07C 67/14 | (2006.01) |
| G03F 7/00 | (2006.01) |
| G03F 7/027 | (2006.01) |
| C07C 69/54 | (2006.01) |
| G03F 7/038 | (2006.01) |

(52) U.S. Cl.
CPC ............... *G03F 7/027* (2013.01); *C07C 67/14* (2013.01); *C07C 69/54* (2013.01); *G03F 7/0382* (2013.01); *C07C 2101/14* (2013.01); *C07C 2103/92* (2013.01)

(58) Field of Classification Search
CPC ............................. G03F 7/027; C07C 69/84
USPC ............................................ 430/285.1, 325
See application file for complete search history.

(56) References Cited

U.S. PATENT DOCUMENTS

| | | | |
|---|---|---|---|
| 4,642,362 A | 2/1987 | Harris et al. | |
| 4,695,615 A | 9/1987 | Leonard et al. | |
| 2002/0012872 A1 | 1/2002 | Kobayashi et al. | |
| 2008/0153031 A1 | 6/2008 | Echigo et al. | |
| 2010/0047709 A1 | 2/2010 | Echigo et al. | |
| 2012/0156615 A1 | 6/2012 | Echigo et al. | |
| 2012/0171615 A1 * | 7/2012 | Echigo et al. | ............ 430/281.1 |

FOREIGN PATENT DOCUMENTS

| | | | | |
|---|---|---|---|---|
| EP | 0196895 | A2 | 10/1986 | |
| EP | 0235935 | A2 | 9/1987 | |
| EP | 0432990 | A2 | 6/1991 | |
| EP | 0490631 | A2 | 6/1992 | |
| JP | H10-310545 | A | 11/1998 | |
| JP | H10310545 | A | 11/1998 | |
| JP | 2000-047018 | A | 2/2000 | |
| JP | 2000047018 | A * | 2/2000 | .............. G02B 5/20 |
| JP | 2004-018421 | A | 1/2004 | |
| JP | 2004018421 | A * | 1/2004 | ............. C07C 69/54 |
| JP | 2005-326838 | A | 11/2005 | |
| JP | 2008-145539 | A | 6/2008 | |
| JP | 2009-173623 | A | 8/2009 | |
| JP | 2010-113117 | A | 5/2010 | |
| JP | 2010-270116 | A | 12/2010 | |
| JP | 2012-224583 | A | 11/2012 | |

(Continued)

OTHER PUBLICATIONS

Ruderisch, A., et al., Studies on sensitivity and etching resistance of calix[4]arene derivatives as negative tone electron beam resists, Microelectronic Engineering, 2003, vol. 67-68, p. 292-299.

Parulekar, S.N., et al., Synthesis of Resorcin[4]arene caitands by ring closing metathesis, Chemical Communications, 2007, No. 46, p. 4901-4903.

Morikawa, O., et al., Sc(OTf)3-catalyzed Cyclooligomerization of 2,4-Dialkoxybenzyl Alcohols. Formation of Resorcin[n]arene Peralkyl Ethers, Polymer Bulletin (Heidelberg, germany), 2005, vol. 53, No. 2, p. 97-107.

Morikawa, O., et al., Conformational properties of C2v-symmetrical resorcin[4]arene tetraethers, Journal of Physical Organic Chemistry, 2006, vol. 19, No. 3, p. 214-218.

(Continued)

*Primary Examiner* — Chanceity Robinson
(74) *Attorney, Agent, or Firm* — Fitch, Even, Tabin & Flannery LLP

(57) ABSTRACT

A cyclic compound of the present invention has a molecular weight of 500 to 5000, and is represented by the following formula (1):

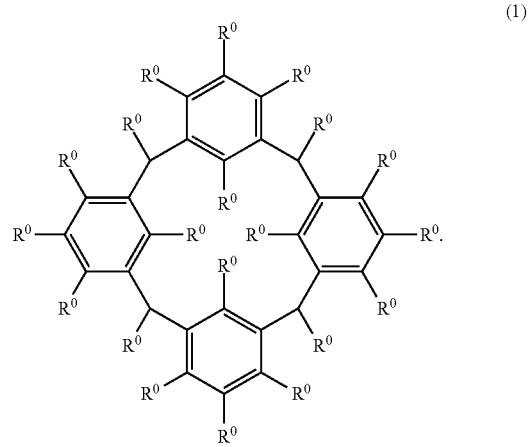

(1)

15 Claims, No Drawings

(56) References Cited

FOREIGN PATENT DOCUMENTS

| KR | 2011-0013819 A | 2/2011 |
| WO | 2011-024916 A1 | 3/2011 |
| WO | 2011-024957 A1 | 3/2011 |
| WO | 2012-133040 A1 | 10/2012 |

OTHER PUBLICATIONS

Balasubramanlan, R., et al., Encapsulation and functionalization of nanoparticles in crosslinked resorcinarene shells, Journal Material Chemistry, 2007, vol. 17, No. 1, p. 105-112.

Mann, G., et al, Structure and stereodynamics of all-cistetramethylcalix[4]arenoctol and -dodecolethers, Supramolecular Chemistry, 1994, vol. 3, No. 2, p. 101-13.

T. Nakayama, M. Nomura, K. Haga, M. Ueda: Bull Chem. Soc. Jpn., 71, 2979 (1998).

Fu, Q and Shi, W., Effect of C-tetramethyl calix[4} resorcinarene acrylate on curing behavior and film properties of thiol-acrylate coating system, Chemical Research in Chinese Universities, 2009, vol. 25, No. 5, p. 760-766.

Huang, Z., and Wang, G., Study of calixarenes, V. Friedel-Crafts reaction of Calizarenes, Chemische Berichte, 1994, vol. 127, No. 3, p. 519-23.

See, K.A., etal., Calixarenes, 26, Selective esterification and selective ester cleavage of claix [4] arenes, Journal of Organic Chemistry, 1991, vol. 56, No. 26, p. 7256-68.

Huang, Z. and Wang, G., Selective Esterification of Calix {4} arenes, Synthetic Communications, 24(1), 1994, p. 11-22.

International Search Report dated Jan. 29, 2013, issued in International Application PCT/JP2012/079528 [translation unavailable].

* cited by examiner

CYCLIC COMPOUND, METHOD FOR PRODUCING THE SAME, RADIATION-SENSITIVE COMPOSITION, AND RESIST PATTERN FORMATION METHOD

CROSS-REFERENCE TO RELATED APPLICATIONS

This Application is a U.S. National Stage Application filed under 35 U.S.C. §371 of International Application PCT/JP 2012/079528, filed Nov. 14, 2012, designating the United States, which claims priority from Japanese Patent Application 2011-253312, filed Nov. 18, 2011, the complete disclosures of which are hereby incorporated herein by reference in their entirety for all purposes.

TECHNICAL FIELD

The present invention relates to a cyclic compound represented by a specific chemical constitution formula, a radiation-sensitive composition containing the same, and a resist pattern formation method using the composition.

BACKGROUND ART

Conventional typical resist materials are polymeric resist materials capable of forming amorphous thin films. Examples thereof include a polymeric resist material such as polymethyl methacrylate, polyhydroxy styrene with an acid dissociation reactive group, or polyalkyl methacrylate. A line pattern of about 45 to 100 nm is formed by irradiating a resist thin film made by coating a substrate with a solution of such a polymer resist material with ultraviolet, far ultraviolet, electron beam, extreme ultraviolet (EUV), and X-ray or the like.

However, because polymeric resist materials have a molecular weight as large as about 10,000 to 100,000 and also wide molecular weight distribution, in lithography using a polymeric resist material, roughness occurs on a fine pattern surface; the pattern dimension becomes difficult to be controlled; and the yield decreases. Therefore, there is a limitation in miniaturization with lithography using a conventional polymeric resist material. In order to make a finer pattern, various low molecular weight resist materials have been proposed.

For example, an alkaline development type negative type radiation-sensitive composition (For example, see Patent Documents 1 and 2) using a low molecular weight polynuclear polyphenolic compound as a main component has been suggested.

As a low molecular weight resist material candidate, an alkaline development type negative type radiation-sensitive composition using a low molecular weight cyclic polyphenolic compound (For example, see Patent Documents 3 and 4, and Non Patent Document 1) as a main component has been suggested.

LIST OF PRIOR ART DOCUMENTS

Patent Document

Patent Document 1: Japanese Patent Application Laid-Open No. 2005-326838

Patent Document 2: Japanese Patent Application Laid-Open No. 2008-145539

Patent Document 3: Japanese Patent Application Laid-Open No. 2009-173623

Patent Document 4: International Publication No. WO 2011/024916

Non Patent Document

Non Patent Document 1: T. Nakayama, M. Nomura, K. Haga, M. Ueda: Bull. Chem. Soc. Jpn., 71, 2979 (1998)

SUMMARY OF INVENTION

Problems to be Solved by Invention

However, alkaline development type negative type radiation-sensitive compositions described in Patent Documents 1 and 2 have insufficient heat resistance and may disable the formation of a resist pattern having a good shape.

In alkaline development type negative type radiation-sensitive compositions described in Patent Documents 3 and 4 and Non Patent Document 1, a low molecular weight cyclic polyphenol compound is expected to provide a resist pattern with small molecular size, high resolution and small roughness due to its low molecular weight. Also, the low molecular weight cyclic polyphenol compound provides high heat resistance even with the low molecular weight, by having a rigid cyclic structure in its backbone. However, the currently known low molecular weight cyclic polyphenol compound has low solubility in a safe solvent used for a semiconductor production process. Therefore, the radiation-sensitive composition containing a low molecular weight cyclic polyphenol compound and a safe solvent has low sensitivity, which may disable the formation of a resist pattern having a good shape. In order to form a resist pattern having high sensitivity and a good shape, an improvement in the low molecular weight cyclic polyphenol compound has been desired.

Then, the object of the present invention is to provide a cyclic compound capable of forming a radiation-sensitive composition which has high solubility in a safe solvent, has high sensitivity, and provides a good resist pattern shape having small roughness, a method for producing the cyclic compound, a radiation-sensitive composition containing the cyclic compound, and a resist pattern formation method using the radiation-sensitive composition.

Means for Solving Problems

The inventors have, as a result of devoted examinations to solve the above problems, found out that a cyclic compound having a specific structure has high solubility in a safe solvent, and is also capable of forming a radiation-sensitive composition which has high sensitivity and provides a good resist pattern shape having small roughness; and reached the present invention.

More specifically, the present invention is as follows.

[1] A cyclic compound having a molecular weight of 500 to 5000 and represented by the formula (1):

(1)

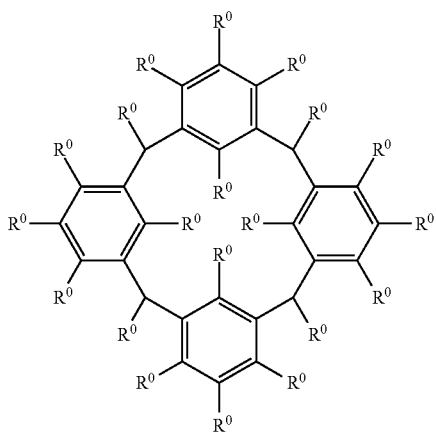

wherein $R^0$ are each independently a hydrogen atom, a hydroxyl group, a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 30 carbon atoms, a substituted or non-substituted alkoxy group having 1 to 20 carbon atoms, a substituted or non-substituted amino group having 0 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 30 carbon atoms, a substituted or non-substituted alkylsilyl group having 1 to 20 carbon atoms, or a group in which each of the groups is bonded to a bivalent group (one or more groups selected from the group consisting of a substituted or non-substituted alkylene group, a substituted or non-substituted allylene group, and an ether group); and at least one of $R^0$ is a monovalent group containing a (meth)acryloyl group.

[2] The cyclic compound according to the above [1], wherein the cyclic compound represented by the formula (1) is represented by the formula (2):

(2)

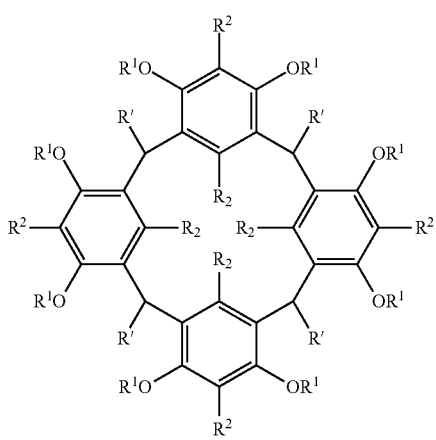

wherein $R^1$ are each independently a hydrogen atom, a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted alkylsilyl group having 1 to 20 carbon atoms, or a substituted or non-substituted alkenyl group having 2 to 20 carbon atoms;

$R^2$ are each independently a hydrogen atom, a cyano group, a nitro group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 30 carbon atoms, a substituted or non-substituted alkoxy group having 1 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 30 carbon atoms, or a substituted or non-substituted alkylsilyl group having 1 to 20 carbon atoms;

$R^1$ are each independently a hydrogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, or a group represented by the following formula (3):

(3)

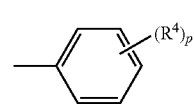

wherein $R^4$ are each independently a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted alkoxy group having 1 to 20 carbon atoms, or a substituted or non-substituted alkylsilyl group having 1 to 20 carbon atoms; p is an integer of 0 to 5; and at least one of $R^1$ is a (meth)acryloyl group.

[3] The cyclic compound according to the above [2], wherein the cyclic compound represented by the formula (2) is represented by the formula (4):

(4)

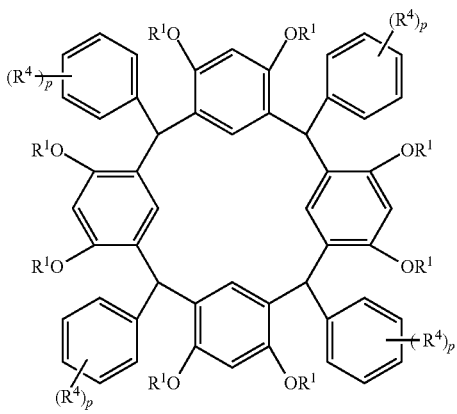

wherein R¹ are each independently a hydrogen atom, a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted alkylsilyl group having 1 to 20 carbon atoms, or a substituted or non-substituted alkenyl group having 2 to 20 carbon atoms;

R⁴ are each independently a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted alkoxy group having 1 to 20 carbon atoms, or a substituted or non-substituted alkylsilyl group having 1 to 20 carbon atoms;

p is an integer of 0 to 5; and at least one of R¹ is a (meth)acryloyl group.

[4] The cyclic compound according to the above [3], wherein the cyclic compound represented by the formula (4) is represented by the formula (5):

(5)

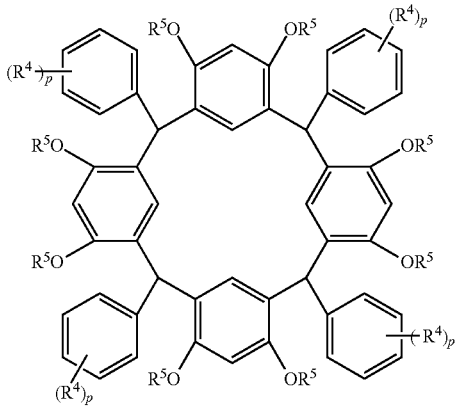

wherein R⁴ are each independently a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted alkoxy group having 1 to 20 carbon atoms, or a substituted or non-substituted alkylsilyl group having 1 to 20 carbon atoms;

p is an integer of 0 to 5; and

R⁵ is a (meth)acryloyl group.

[5] A method for producing the cyclic compound according to any one of the above [1] to [4], comprising the steps of:

a condensation reaction of one or more aldehyde compounds (A1) with one or more phenolic compounds (A2) to obtain a cyclic compound (A); and a dehydrohalogenation reaction of the cyclic compound (A) with one or more (meth)acryloyl halides.

[6] The method for producing the cyclic compound according to the above [5], wherein:

the aldehyde compound (A1) has 1 to 4 formyl groups and has 1 to 59 carbon atoms; and the phenolic compound (A2) has 1 to 3 phenolic hydroxyl groups and has 6 to 15 carbon atoms.

[7] A radiation-sensitive composition comprising a solid component containing the cyclic compound according to any one of the above [1] to [4] and a solvent.

[8] The radiation-sensitive composition according to the above [7], comprising 1 to 80% by weight of the solid component.

[9] The radiation-sensitive composition according to the above [7] or [8], wherein a content of the cyclic compound is 50 to 99.999% by weight based on a total weight of the solid component.

[10] The radiation-sensitive composition according to any one of the above [7] to [9], further comprising an acid generating agent (C) which directly or indirectly generates acid upon exposure to any radiation selected from the group consisting of visible light, ultraviolet, excimer laser, electron beam, extreme ultraviolet (EUV), X-ray, and ion beam.

[11] The radiation-sensitive composition according to any one of the above [7] to [10], further comprising an acid crosslinking agent (G).

[12] The radiation-sensitive composition according to any one of the above [7] to [11], further comprising an acid diffusion controlling agent (E).

[13] The radiation-sensitive composition according to any one of the above [7] to [12], wherein the solid component comprises 50 to 99.4% by weight of the cyclic compound, 0.001 to 49% by weight of an acid generating agent (C), 0.5 to 49% by weight of an acid crosslinking agent (G), and 0.001 to 49% by weight of an acid diffusion controlling agent (E).

[14] The radiation-sensitive composition according to any one of the above [7] to [13], forming an amorphous film by spin coating.

[15] The radiation-sensitive composition according to the above [14], wherein a dissolution rate of the amorphous film into a developing solution at 23° C. is 10 angstrom/sec or more.

[16] The radiation-sensitive composition according to the above [14] or [15], wherein a dissolution rate of the amorphous film into a developing solution is 5 angstrom/sec or less after exposed to KrF excimer laser, extreme ultraviolet, electron beam, or X-ray, or after heated at 20 to 250° C.

[17] A method for forming a resist pattern, comprising the steps of:

forming a resist film by coating a substrate with the radiation-sensitive composition according to any one of the above [7] to [16];

exposing the resist film; and developing the exposed resist film.

Advantages of Invention

The present invention can provide a cyclic compound having high solubility in a safe solvent and capable of forming a radiation-sensitive composition which has high sensitivity and provides a good resist pattern shape having small roughness, a method for producing the cyclic compound, a radiation-sensitive composition containing the cyclic compound, and a resist pattern formation method using the radiation-sensitive composition.

MODE FOR CARRYING OUT INVENTION

Hereinafter, an embodiment of the present invention (hereinafter, also referred to as "present embodiment") will be described in detail. The following embodiment is given in order to illustrate the present invention. The present invention is not limited to only the embodiment.

(Cyclic Compound and Production Method Thereof)

A cyclic compound of the present embodiment is a cyclic compound having a molecular weight of 500 to 5000 and represented by the following formula (1). The cyclic compound of the present embodiment is useful as a resist material.

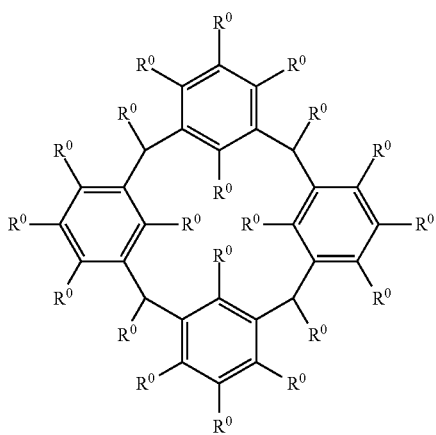

(1)

In the formula (1), $R^0$ are each independently a hydrogen atom, a hydroxyl group, a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 30 carbon atoms, a substituted or non-substituted alkoxy group having 1 to 20 carbon atoms, a substituted or non-substituted amino group having 0 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 30 carbon atoms, a substituted or non-substituted alkylsilyl group having 1 to 20 carbon atoms, or a group in which each of the groups is bonded to a bivalent group (one or more groups selected from the group consisting of a substituted or non-substituted alkylene group, a substituted or non-substituted allylene group, and an ether group); and at least one of $R^0$ is a monovalent group containing a (meth)acryloyl group.

At least one of $R^0$ is a monovalent group containing a (meth)acryloyl group, and thereby the cyclic compounds can be anionically polymerized by an acid. As a result, the sensitivity of the radiation-sensitive composition (resist) containing the cyclic compound of the present embodiment can be further improved. Particularly, in extreme ultraviolet (EUV) lithography, the high sensitivity of the resist is made indispensable for improvement in productivity of a semiconductor device. The cyclic compound of the present embodiment is extremely useful.

Unless the circumstances are exceptional, "substitution" in the present specification means that one or more hydrogen atoms in a functional group are substituted with a halogen atom, a hydroxyl group, a cyano group, a nitro group, a heterocyclic group, a linear aliphatic hydrocarbon group having 1 to 20 carbon atoms, a branched aliphatic hydrocarbon group having 3 to 20 carbon atoms, a cyclic aliphatic hydrocarbon group having 3 to 20 carbon atoms, an aryl group having 6 to 20 carbon atoms, an aralkyl group having 7 to 30 carbon atoms, an alkoxy group having 1 to 20 carbon atoms, an amino group having 0 to 20 carbon atoms, an alkenyl group having 2 to 20 carbon atoms, an acyl group having 1 to 20 carbon atoms, an alkoxycarbonyl group having 2 to 20 carbon atoms, an alkyloyloxy group having 1 to 20 carbon atoms, an aryloyloxy group having 7 to 30 carbon atoms, or an alkylsilyl group having 1 to 20 carbon atoms.

Examples of the non-substituted heterocyclic group include, but not particularly limited to, a pyridyl group, a bipyridyl group, a pyrrolidyl group, a pyrazolyl group, an imidazolyl group, an isoxazolyl group, an isothiazolyl group, a piperidyl group, a piperazyl group, a morpholyl group, a thiomorpholyl group, a triazolyl group, and a tetrazole group.

Examples of the substituted heterocyclic group include, but not particularly limited to, an N-methylpyridyl group, an N-fluoropyridyl group, an N-hydroxypyridyl group, an N-cyanopyridyl group, a methylbipyridyl group, a methylpyrrolidyl group, a methylpyrazolyl group, a methylimidazolyl group, a methylisoxazolyl group, a methylisothiazolyl group, a methylpiperidyl group, a methylpiperazyl group, a methylmorpholyl group, a methylthiomorpholyl group, a methyltriazole group, and a methyltetrazole group.

Examples of the non-substituted linear aliphatic hydrocarbon group having 1 to 20 carbon atoms include, but not particularly limited to, a methyl group, an ethyl group, a propyl group, a butyl group, a pentyl group, a hexyl group, an octyl group, a decyl group, a dodecyl group, a hexadecyl group, and an octadecyl group.

Examples of the substituted linear aliphatic hydrocarbon group having 1 to 20 carbon atoms include, but not particularly limited to, a fluoromethyl group, a 2-hydroxyethyl group, a 3-cyanopropyl group, and a 20-nitrooctadecyl group.

Examples of the non-substituted branched aliphatic hydrocarbon group having 3 to 20 carbon atoms include, but not particularly limited to, an isopropyl group, an isobutyl group, a tertiary-butyl group, a neopentyl group, a 2-hexyl group, a 2-octyl group, a 2-decyl group, a 2-dodecyl group, a 2-hexadecyl group, and a 2-octadecyl group.

Examples of the substituted branched aliphatic hydrocarbon group having 3 to 20 carbon atoms include, but not particularly limited to, a 1-fluoroisopropyl group and a 1-hydroxy-2-octadecyl group.

Examples of the non-substituted cyclic aliphatic hydrocarbon group having 3 to 20 carbon atoms include, but not particularly limited to, a cyclopropyl group, a cyclobutyl group, a cyclopentyl group, a cyclohexyl group, a cyclooctyl group, a cyclodecyl group, a cyclododecyl group, a cyclohexadecyl group, and a cyclooctadecyl group.

Examples of the substituted cyclic aliphatic hydrocarbon group having 3 to 20 carbon atoms include, but not particularly limited to, a 2-fluorocyclopropyl group and a 4-cyanocyclohexyl group.

Examples of the non-substituted aryl group having 6 to 20 carbon atoms include, but not particularly limited to, a phenyl group and a naphthyl group.

Examples of the substituted aryl group having 6 to 20 carbon atoms include, but not particularly limited to, a 4-methylphenyl group and a 6-fluoronaphthyl group.

Examples of the non-substituted aralkyl group having 7 to 30 carbon atoms include, but not particularly limited to, a methylphenyl group, an ethylphenyl group, a methylnaphthyl group, and a dimethylnaphthyl group.

Examples of the substituted aralkyl group having 7 to 30 carbon atoms include, but not particularly limited to, a 4-fluoro-3-methylphenyl group.

Examples of the non-substituted alkoxy group having 1 to 20 carbon atoms include, but not particularly limited to, a methoxy group, an ethoxy group, a propoxy group, a butoxy group, a pentyloxy group, a hexyloxy group, an octyloxy group, a decyloxy group, a dodecyloxy group, a hexadecyloxy group, and an octadecyloxy group.

Examples of the substituted alkoxy group having 1 to 20 carbon atoms include, but not particularly limited to, a chloromethoxy group and a bromoethoxy group.

Examples of the non-substituted amino group having 0 to 20 carbon atoms include, but not particularly limited to, an amino group, a methylamino group, a dimethylamino group, an ethylamino group, a diethylamino group, a dipropylamino group, and a dibutylamino group.

Examples of the substituted amino group having 0 to 20 carbon atoms include, but not particularly limited to, a chloromethylamino group and a dibromomethylamino group.

Examples of the non-substituted alkenyl group having 2 to 20 carbon atoms include, but not particularly limited to, a vinyl group, a propynyl group, a butynyl group, a pentynyl group, a hexynyl group, an octynyl group, a decynyl group, a dodecynyl group, a hexadecynyl group, and an octadecynyl group.

Examples of the substituted alkenyl group having 2 to 20 carbon atoms include, but not particularly limited to, a chloropropynyl group.

Examples of the non-substituted acyl group having 1 to 20 carbon atoms include, but not particularly limited to, a formyl group, an acetyl group, a propanoyl group, a butanoyl group, a pentanoyl group, a hexanoyl group, an octanoyl group, a decanoyl group, a dodecanoyl group, a hexadecanoyl group, and a benzoyl group, in addition to the (meth)acryloyl group.

Examples of the substituted acyl group having 1 to 20 carbon atoms include, but not particularly limited to, a chloroacetyl group.

Examples of the non-substituted alkoxycarbonyl group having 2 to 20 carbon atoms include, but not particularly limited to, a methoxycarbonyl group, an ethoxycarbonyl group, a propoxycarbonyl group, a butoxycarbonyl group, a pentyloxycarbonyl group, a hexyloxycarbonyl group, an octyloxycarbonyl group, a decyloxycarbonyl group, a dodecyloxycarbonyl group, and a hexadecyloxycarbonyl group.

Examples of the substituted alkoxycarbonyl group having 2 to 20 carbon atoms include, but not particularly limited to, a chloromethoxycarbonyl group.

Examples of the non-substituted alkyloyloxy group having 1 to 20 carbon atoms include, but not particularly limited to, a methoxycarbonyloxy group, an ethoxycarbonyloxy group, a propoxycarbonyloxy group, a butoxycarbonyloxy group, a pentyloxycarbonyloxy group, a hexyloxycarbonyloxy group, an octyloxycarbonyloxy group, a decyloxycarbonyloxy group, a dodecyloxycarbonyloxy group, and a hexadecyloxycarbonyloxy group.

Examples of the substituted alkyloyloxy group having 1 to 20 carbon atoms include, but not particularly limited to, a chloromethoxycarbonyloxy group.

Examples of the non-substituted aryloyloxy group having 7 to 30 carbon atoms include, but not particularly limited to, a benzoyloxy group and a naphthylcarbonyloxy group.

Examples of the substituted aryloyloxy group having 7 to 30 carbon atoms include, but not particularly limited to, a chlorobenzoyloxy group.

Examples of the non-substituted alkylsilyl group having 1 to 20 carbon atoms include, but not particularly limited to, a methylsilyl group, an ethylsilyl group, a propylsilyl group, a butylsilyl group, a pentylsilyl group, a hexylsilyl group, an octylsilyl group, a decylsilyl group, a dodecylsilyl group, a hexadecylsilyl group, and an octadecylsilyl group.

Examples of the substituted alkylsilyl group having 1 to 20 carbon atoms include, but not particularly limited to, a chloromethylsilyl group.

Examples of the monovalent group containing a (meth) acryloyl group include, but not particularly limited to, a (meth)acryloyl group, a (meth)acryloyloxy group, a linear aliphatic hydrocarbon group having 1 to 6 carbon atoms substituted with the (meth)acryloyl group, a branched aliphatic hydrocarbon group having 3 to 6 carbon atoms substituted with the (meth)acryloyl group, a cyclic aliphatic hydrocarbon group having 3 to 6 carbon atoms substituted with the (meth)acryloyl group, or an aryl group having 6 carbon atoms substituted with the (meth)acryloyl group.

The cyclic compound represented by the formula (1) is preferably a compound represented by the formula (2).

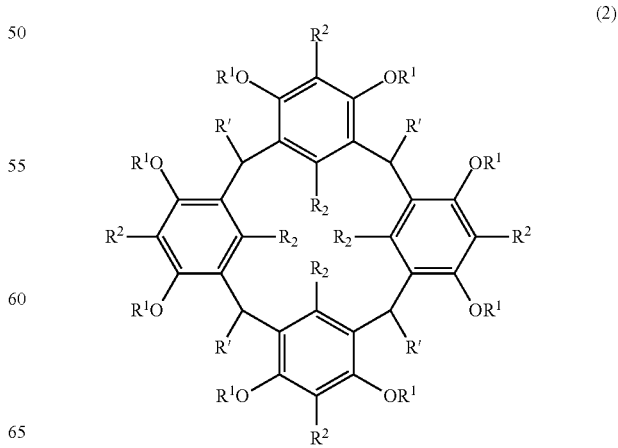

(2)

In the formula (2), $R^1$ are each independently a hydrogen atom, a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted alkylsilyl group having 1 to 20 carbon atoms, or a substituted or non-substituted alkenyl group having 2 to 20 carbon atoms; $R^2$ are each independently a hydrogen atom, a cyano group, a nitro group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 30 carbon atoms, a substituted or non-substituted alkoxy group having 1 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 30 carbon atoms, or a substituted or non-substituted alkylsilyl group having 1 to 20 carbon atoms; $R^1$ are each independently a hydrogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, or a group represented by the following formula (3):

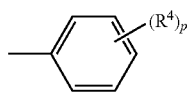

(3)

In the formula (3), $R^4$ are each independently a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted alkoxy group having 1 to 20 carbon atoms, or a substituted or non-substituted alkylsilyl group having 1 to 20 carbon atoms; p is an integer of 0 to 5; and at least one of $R^1$ is a (meth)acryloyl group.

The compound represented by the formula (2) is more preferably a compound represented by the formula (4):

The compound represented by the formula (4) has high solubility in a safe solvent, and can form a radiation-sensitive composition which has high sensitivity and provides a good resist pattern shape having small roughness.

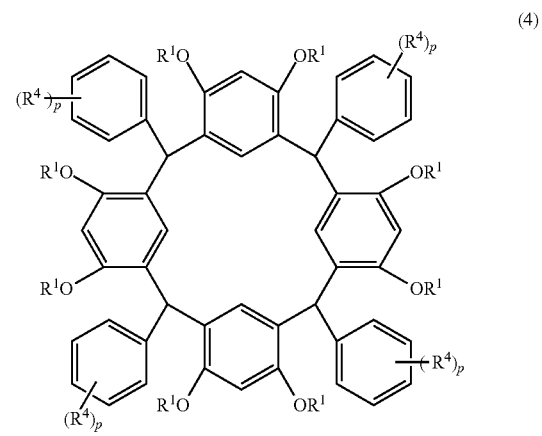

(4)

In the formula (4), $R^1$, $R^4$ and p are the same as above.

Further, the compound represented by the formula (4) is still more preferably a compound represented by the formula (5):

The compound represented by the formula (5) has high solubility in a safe solvent, and can form a radiation-sensitive composition which has high sensitivity and provides a good resist pattern shape having small roughness.

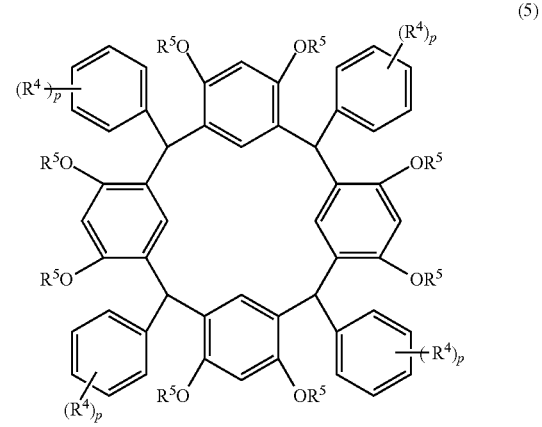

(5)

In the formula (5), $R^4$ and p are the same as above, and $R^5$ is a (meth)acryloyl group.

The compound represented by the formula (4) is yet still more preferably a compound represented by the formula (6) or formula (7):

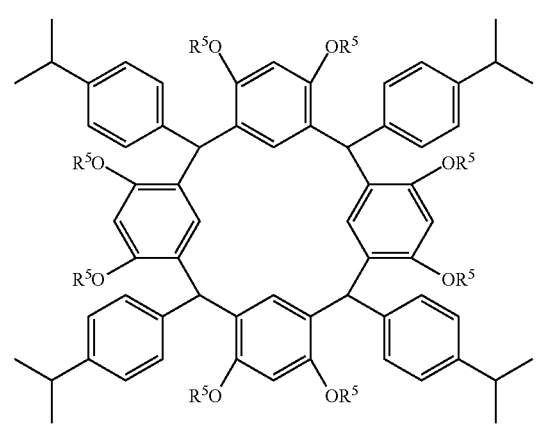

(6)

In the formula (6), $R^5$ is the same as above.

(7)

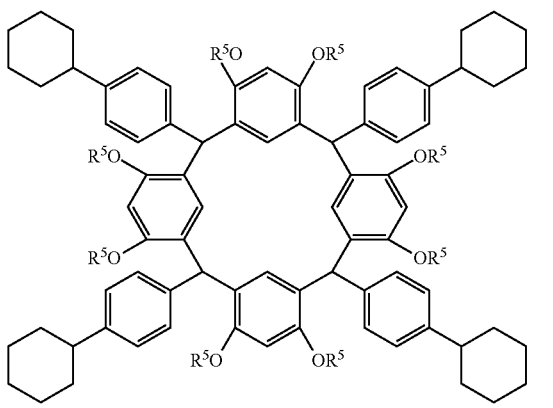

In the formula (7), $R^5$ is the same as above.

The compound represented by the formula (6) or (7) has higher solubility in a safe solvent, and can form a radiation-sensitive composition which has higher sensitivity and provides a resist pattern having a better shape having smaller roughness.

The molecular weight of the cyclic compound represented by the formula (1) is 500 to 5000, preferably 800 to 2000, and more preferably 1000 to 2000. The above range can improve the resolution while maintaining the film forming property required when a resist is formed.

The cyclic compound of the present embodiment can be the cis form and the trans form, but may be any one of forms or mixture of them. When the cyclic compound of the present embodiment is used as a resist component of a radiation-sensitive composition, it is preferable to use only one of the cis form and the trans form, because the uniformity of the component within the resist film is high. A method for obtaining a cyclic compound having only one of the cis form and the trans form can be conducted by a publicly known methods such as separation by column chromatography or preparative liquid chromatography, and optimization of a reaction solvent and reaction temperature or the like upon production.

The cyclic compound of the present embodiment is obtained by a production method including the steps of: a condensation reaction of one or more aldehyde compounds (A1) with one or more phenolic compounds (A2) to obtain a cyclic compound (A); and a dehydrohalogenation reaction of the cyclic compound (A) with one or more (meth)acryloyl halides.

Preferably, the cyclic compound of the present embodiment is obtained by a dehydrohalogenation reaction of a cyclic compound (A) obtained by a condensation reaction of one or more compounds selected from various aromatic aldehyde compounds (A1A) with one or more compounds selected from various phenol compounds (A2), with one or more compounds selected from various (meth)acryloyl halides (A3).

The cyclic compound of the present embodiment can also be obtained by a condensation reaction of a phenol compound (A2A) obtained by a dehydrohalogenation reaction of one or more compounds selected from various phenol compounds (A2) with one or more compounds selected from various (meth)acryloyl halides (A3), with one or more compounds selected from various aldehyde compounds (A1).

The aldehyde compound (A1) preferably has 1 to 59 carbon atoms. The aldehyde compound (A1) preferably has 1 to 4 formyl groups. The aldehyde compound (A1) is selected from an aromatic aldehyde compound (A1A) and an aliphatic aldehyde compound (A1B). The aromatic aldehyde compound (A1A) is preferably a benzaldehyde compound having 7 to 24 carbon atoms. Examples of the aromatic aldehyde compound (A1A) include, but not particularly limited to, benzaldehyde, methylbenzaldehyde, dimethylbenzaldehyde, ethylbenzaldehyde, propylbenzaldehyde, butylbenzaldehyde, ethylmethylbenzaldehyde, isopropylmethylbenzaldehyde, diethylbenzaldehyde, anisaldehyde, naphthaldehyde, anthraldehyde, cyclopropylbenzaldehyde, cyclobutylbenzaldehyde, cyclopentylbenzaldehyde, cyclohexylbenzaldehyde, phenylbenzaldehyde, naphthylbenzaldehyde, adamantylbenzaldehyde, norbornylbenzaldehyde, lactylbenzaldehyde, isopropylbenzaldehyde, normalpropylbenzaldehyde, bromobenzaldehyde, dimethylaminobenzaldehyde, hydroxybenzaldehyde, dihydroxybenzaldehyde, and trihydroxybenzaldehyde. Isopropylbenzaldehyde, normalpropylbenzaldehyde, cyclohexylbenzaldehyde, and phenylbenzaldehyde are preferable, and cyclohexylbenzaldehyde and 4-isopropylbenzaldehyde are more preferable. The aromatic aldehyde compound (A1A) may have a linear or branched alkyl group having 1 to 4 carbon atoms, a cyano group, a hydroxyl group, and a halogen or the like, within the range of not deteriorating the effect of the present invention. The aromatic aldehyde compound (A1A) may be used alone or in combination of two or more kinds.

The aliphatic aldehyde compound (A1B) is preferably a compound having 1 to 24 carbon atoms. Examples of the aliphatic aldehyde compound (A1B) include, but not particularly limited to, methanal, ethanal, propanal, isopropanal, butanal, isobutanal, t-butanal, pentanal, isopentanal, neopentanal, hexanal, isohexanal, octanal, decanal, dodecanal, undecenal, cyclopropanecarboxyaldehyde, cyclobutanecarboxyaldehyde, and cyclohexanecarboxyaldehyde. Isobutanal, t-butanal, pentanal, isopentanal, neopentanal, hexanal, isohexanal, octanal, decanal, dodecanal, cyclopropanecarboxyaldehyde, cyclobutanecarboxyaldehyde, and cyclohexanecarboxyaldehyde are preferable, and octanal, decanal, dodecanal, and cyclohexanecarboxyaldehyde are more preferable. The aliphatic aldehyde compound (A1B) may have a cyano group, a hydroxyl group, and a halogen or the like, within the range of not deteriorating the effect of the present invention. The aliphatic aldehyde compound (A1B) may be used alone or in combination of two or more kinds.

The suitable phenolic compound (A2) preferably has 6 to 15 carbon atoms, and preferably has 1 to 3 phenolic hydroxyl groups. Examples of the phenolic compound (A2) include, but not particularly limited to, phenol, catechol, resorcinol, hydroquinone, and pyrogallol. Resorcinol, and pyrogallol are preferable, and resorcinol is more preferable. The phenolic compound (A2) may have a linear or branched alkyl group having 1 to 4 carbon atoms, a cyano group, a hydroxyl group, and a halogen or the like, within the range of not deteriorating the effect of the present invention. The phenolic compound (A2) may be used alone or in combination of two or more kinds.

The (meth)acryloyl halide (A3) is preferably (meth)acryloyl chloride, (meth)acryloyl bromide, and (meth)acryloyl iodide, for example. The (meth)acryloyl halide (A3) may have a linear or branched alkyl group having 1 to 4 carbon atoms, a cyano group, a hydroxyl group, and a halogen or the like, within the range of not deteriorating the effect of the present invention. The (meth)acryloyl halide (A3) may be used alone or in combination of two or more kinds.

For example, specifically, the cyclic compound of the present embodiment can be produced by the following method. For example, 0.1 to 10 moles of the phenolic compound (A2) is reacted per mole of the aldehyde compound (A1) at 60 to 150° C. for about 0.5 to 20 hours in the presence of an acid catalyst (such as hydrochloric acid, sulfuric acid, or para-toluene sulfonic acid) in an organic solvent such as methanol or ethanol. Then, the reaction product is filtered, washed with alcohols such as methanol, washed with water, filtered to separate, and then dried, to obtain a cyclic compound (A) having a molecular weight of preferably 700 to 5000. The cyclic compound (A) can also be obtained by using a basic catalyst (such as sodium hydroxide, barium hydroxide, or 1,8-diazabicyclo[5.4.0]undecene-7) instead of the acid catalyst and reacting in the same way. Furthermore, the cyclic compound (A) can also be produced by treating the above aldehyde compound (A1) with hydrogen halide or halogen gas into dihalide, and reacting the isolated dihalide with the phenolic compound (A2).

Then, 1 mol of the cyclic compound (A) and 0.1 to 10 mol of the (meth)acryloyl halide (A3) are allowed to react at 0 to 150° C. for about 0.5 to 20 hours in an organic solvent such as N-methyl-2-pyrrolidone, in the presence of a basic catalyst (triethylamine, ammonia, or sodium hydroxide or the like). By this reaction, a phenolic hydroxyl group in the cyclic compound (A) can be converted to a (meth)acryloyl group. Then, the reaction product is filtered, washed with alcohols such as methanol, washed with water, filtered to separate, and then dried, to obtain the cyclic compound represented by formula (1).

It is more preferable to use two or more of at least one of the aldehyde compound (A1) or the phenolic compound (A2) because the solubility of the resulting cyclic compound in a semiconductor safe solvent improves.

In the method for producing the cyclic compound, in order to improve the purity of the cyclic compound, and to reduce the remaining metal amount, a purification step may be conducted if required. When an acid catalyst and a co-catalyst remain, the storage stability of a radiation-sensitive composition generally decreases. When a basic catalyst remains, the sensitivity of a radiation-sensitive composition generally decreases. Therefore, purification for the purpose of reducing these catalysts may be conducted.

The purification method can be conducted by any publicly known method unless a cyclic compound is modified. Examples thereof include, but not particularly limited to, methods of washing with water, washing with an acid aqueous solution, washing with a basic aqueous solution, treating with an ion exchange resin, and treating by silica gel column chromatography. It is more preferable to conduct these purification methods in combination of two or more kinds. It is possible to arbitrarily select the optimal one for the acid aqueous solution, the basic aqueous solution, the ion exchange resin, and the silica gel column chromatography, according to the amount and kind of metal, acidic compound and basic compound to be removed, and the kind of cyclic compound to be purified or the like. Examples of the acid aqueous solution include aqueous solutions of hydrochloric acid, nitric acid, and acetic acid with a concentration of 0.01 to 10 mol/L. Examples of the basic aqueous solution include an aqueous solution of ammonia with a concentration of 0.01 to 10 mol/L. Examples of the ion exchange resin include a cation exchange resin such as Amberlyst 15J-HG Dry manufactured by Organo. Drying may be conducted after purification. Drying can be conducted by a publicly known method. Examples of the method include, but not particularly limited to, methods of vacuum drying and hot air drying under the condition where a cyclic compound is not modified.

When the cyclic compound of the present embodiment is used as the component of the radiation-sensitive composition, an amorphous film can be formed by spin coating. The cyclic compound of the present embodiment can be applied to a typical semiconductor production process.

The cyclic compound of the present embodiment is useful as a negative type resist material which becomes a hardly soluble compound in a developing solution by being irradiated with KrF excimer laser, extreme ultraviolet, electron beam, or X-ray. A mechanism in which the cyclic compound of the present embodiment is a compound hardly soluble in a developing solution is not clear. However, by irradiating the cyclic compound with KrF excimer laser, extreme ultraviolet, electron beam, or X-ray, a condensation reaction among the compounds is considered to be induced to provide a compound hardly soluble in an alkaline developing solution. Thus, a resist pattern obtained by using the cyclic compound of the present embodiment has very small line edge roughness (LER).

Further, the cyclic compound of the present embodiment can be used as a main component of a negative type radiation-sensitive composition. Moreover, the cyclic compound can be added to a radiation-sensitive composition as an additive agent for improving sensitivity and etching resistance, for example. In this case, the amount of the cyclic compound of the present embodiment used as an additive agent is preferably 1 to 49.999% by weight of the total weight of the solid component of the radiation-sensitive composition.

The glass transition temperature of the cyclic compound of the present embodiment is preferably 100° C. or more, more preferably 120° C. or more, still more preferably 140° C. or more, and particularly preferably 150° C. or more. By having the glass transition temperature within the above range, in a semiconductor lithography process, it has heat resistance capable of maintaining the pattern shape, and improved performance such as high resolution.

The crystallization heat generation amount obtained by differential scanning calorimetrical analysis of the glass transition temperature of the cyclic compound of the present embodiment is preferably less than 20 J/g. In the cyclic compound of the present embodiment, (crystallization temperature)−(glass transition temperature) is preferably 70° C. or more, more preferably 80° C. or more, still more preferably 100° C. or more, and particularly preferably 130° C. or more. When the crystallization heat generation amount is less than 20 J/g or (crystallization temperature)−(glass transition temperature) is within the above range, by spin coating with a radiation-sensitive composition, an amorphous film is easily formed; the film forming property required for a resist can be maintained over an extended period of time; and the resolution can be further improved.

In the present embodiment, the crystallization heat generation amount, the crystallization temperature, and the glass transition temperature can be obtained by differential scanning calorimetrical analysis using DSC/TA-50WS manufactured by Shimadzu Corporation as follows. About 10 mg of the sample is placed in a non-sealed container made of aluminum, and the temperature is raised to the melting point or more at the rate of temperature rise of 20° C./min in a nitrogen gas stream (50 mL/min). After quenching, again the temperature is raised to the melting point or more at the rate of temperature rise of 20° C./min in a nitrogen gas stream (30 mL/min). After further quenching, again the temperature is raised to 400° C. at the rate of temperature rise of 20° C./min in a nitrogen gas stream (30 mL/min). The temperature at the middle point of the step of the baseline stepwisely changed (where the specific heat is changed into the half) is defined as the glass transition temperature (Tg), and the temperature at the subsequently appearing heat generation peak is defined as the crystallization temperature. The heat generation amount is obtained from the area of the region surrounded by the heat generation peak and the baseline, as the crystallization heat generation amount.

The cyclic compound of the present embodiment preferably has a low sublimation property under normal pressure at 100° C. or less, preferably 120° C. or less, more preferably 130° C. or less, still more preferably 140° C. or less, and particularly preferably 150° C. or less. Herein, the low sublimation property means that the weight decrease after being kept at a predetermined temperature for 10 minutes in thermogravimetrical analysis is 10% or less, preferably 5% or less, more preferably 3% or less, still more preferably 1% or less, and particularly preferably 0.1% or less. Contamination of an exposure equipment by outgas upon exposure can be prevented by the low sublimation property. Also, a good pattern shape with low LER can be obtained.

The cyclic compound of the present embodiment is preferably F<3.0 (F represents total atom number/(total carbon atom number-total oxygen atom number)), and more preferably F<2.5. By meeting the above condition, the cyclic compound of the present embodiment has excellent dry etching resistance.

The cyclic compound of the present embodiment dissolves in a solvent selected from propylene glycol monomethyl ether acetate (PGMEA), propylene glycol monomethyl ether (PGME), cyclohexanone (CHN), cyclopentanone (CPN), 2-heptanone, anisole, butyl acetate, ethyl propionate, and ethyl lactate, and showing the highest dissolving ability to the cyclic compound, in preferably 1% by mass or more, more preferably 5% by mass or more, and still more preferably 10% by mass or more at 23° C. Among these, the cyclic compound of the present embodiment dissolves in a solvent selected from PGMEA, PGME and CHN, and showing the highest dissolving ability to the cyclic compound, in preferably 20% by mass or more at 23° C., and particularly preferably in PGMEA in 20% by mass or more at 23° C. When the above conditions are met, the use of the cyclic compound of the present embodiment in a semiconductor production process in the actual production becomes possible.

A nitrogen atom may be introduced into the cyclic compound of the present embodiment, within the range of not deteriorating the effect of the present invention. The percentage of the number of nitrogen atoms to the number of all constituent atoms of the cyclic compound is preferably 0.1 to 40%, more preferably 0.1 to 20%, still more preferably 0.1 to 10%, and particularly preferably 0.1 to 5%. When the percentage of the number of nitrogen atoms to the number of all constituent atoms of the cyclic compound is within the above range, the line edge roughness of the obtained resist pattern can be reduced. The nitrogen atom introduced into the cyclic compound of the present embodiment is preferably a secondary nitrogen atom or a tertiary nitrogen atom, and more preferably a tertiary nitrogen atom.

A crosslinking reactive group initiating a crosslinking reaction by visible light, ultraviolet, excimer laser, electron beam, extreme ultraviolet (EUV), X-ray, and ion beam irradiation or a chemical reaction induced thereby may be introduced into the cyclic compound of the present embodiment, within the range of not deteriorating the effect of the present invention. The introduction of a crosslinking reactive group into the cyclic compound of the present embodiment is conducted by, for example, reacting the cyclic compound with the crosslinking reactive group introducing agent in the presence of a basic catalyst. Examples of the crosslinking reactive group include, but not particularly limited to, a carbon-carbon multiple bond, an epoxy group, an azide group, a halogenated phenyl group, and a chloromethyl group. Examples of the crosslinking reactive group introducing agent include, but not particularly limited to, an acid having such a crosslinking reactive group, acid chloride, acid anhydride, a carboxylic acid derivative such as dicarbonate, and alkyl halide. A radiation-sensitive composition containing a cyclic compound having a crosslinking reactive group is also useful as a nonpolymeric radiation-sensitive composition with high resolution, high heat resistance, and solvent solubility.

A nonacid dissociation functional group may be introduced into at least one phenolic hydroxyl group of the cyclic compound of the present embodiment, within the range of not deteriorating the effect of the present invention. The nonacid dissociation functional group refers to a characteristic group not cleaving in the presence of an acid and not generating an alkali soluble group. Examples of the nonacid dissociation functional group include a functional group selected from the group consisting of an alkyl group having C1 to 20, a cycloalkyl group having C3 to 20, an aryl group having C6 to 20, an alkoxyl group having C1 to 20, a cyano group, a nitro group, a hydroxyl group, a heterocyclic group, halogen, a carboxyl group, alkylsilane of C1 to 20, and a derivative thereof, which are not degraded by action of an acid.

A naphthoquinone diazide ester group may be introduced into at least one phenolic hydroxyl group of the cyclic compound of the present embodiment, within the range of not deteriorating the effect of the present invention. A cyclic compound having a naphthoquinone diazide ester group introduced into at least one phenolic hydroxyl group of the cyclic compound, as a main component itself, can be used as a main component of a negative type radiation-sensitive composition. Moreover, the cyclic compound can be used as a main component of a positive type radiation-sensitive composition, and can be added to a radiation-sensitive composition, as an acid generating agent and an additive agent.

An acid generating functional group generating an acid by irradiation of radiation may be introduced into at least one phenolic hydroxyl group of the cyclic compound of the present embodiment, within the range of not deteriorating the effect of the present invention. A cyclic compound having an acid generating functional group introduced into at least one phenolic hydroxyl group of the cyclic compound, as a main component itself, can be used as a main component of a negative type radiation-sensitive composition. Moreover, the cyclic compound can be added to a radiation-sensitive composition as an additive agent.

(Radiation-Sensitive Composition)

The radiation-sensitive composition of the present embodiment contains a solid component containing the above cyclic compound and, a solvent. The radiation-sensitive composition of the present embodiment comprises preferably 1 to 80% by weight of the solid component. Furthermore, the content of the cyclic compound is preferably 50 to 99.999% by weight based on the total weight of the solid component.

The radiation-sensitive composition of the present embodiment can form an amorphous film by spin coating. The dissolution rate of the amorphous film formed by spin coating the radiation-sensitive composition of the present embodiment in a developing solution at 23° C. is preferably 10 angstrom/sec or more, more preferably 10 to 10000 angstrom/sec, and still more preferably 100 to 1000 angstrom/sec. When the dissolution rate of the radiation-sensitive composition of the present embodiment is 10 angstrom/sec or more, it can dissolve in the developing solution to be a resist.

When the radiation-sensitive composition of the present embodiment has the dissolution rate of 10000 angstrom/sec or less, the resolution may improve. It is presumed that this is because due to the change in the solubility before and after exposure of the cyclic compound, contrast at the interface between the unexposed portion being dissolved in a developing solution and the exposed portion not being dissolved in a developing solution is increased. There are reduction effects of LER and defect.

The dissolution rate of the portion exposed by radiation such as KrF excimer laser, extreme ultraviolet, electron beam or X-ray, of the amorphous film formed by spin coating with the radiation-sensitive composition of the present embodiment, in a developing solution at 23° C. is preferably 5 angstrom/sec or less, more preferably 0.05 to 5 angstrom/sec, and still more preferably 0.0005 to 5 angstrom/sec. When the radiation-sensitive composition of the present embodiment has the dissolution rate of 5 angstrom/sec or less, the radiation-sensitive composition is insoluble in a developing solution, and is suitably used for a resist. When the radiation-sensitive composition of the present embodiment has the dissolution rate of 0.0005 angstrom/sec or more, the resolution may improve. It is presumed that this is because the micro surface portion of the cyclic compound dissolves and LER is reduced. There is also a reduction effect of defect.

As described above, the radiation-sensitive composition of the present embodiment preferably contains 1 to 80% by weight of the solid component and 20 to 99% by weight of the solvent, more preferably contains 1 to 50% by weight of the solid component and 50 to 99% by weight of the solvent, still more preferably 2 to 40% by weight of the solid component and 60 to 98% by weight of the solvent, and particularly preferably 2 to 10% by weight of the solid component and 90 to 98% by weight of the solvent.

In the radiation-sensitive composition of the present embodiment, the amount of the above cyclic compound is preferably 50 to 99.4% by weight of the total weight of the solid component (summation of optionally used solid component such as the above cyclic compound, acid generating agent (C), acid crosslinking agent (G), acid diffusion controlling agent (E), and other component (F) to be described below, hereinafter the same), more preferably 55 to 90% by weight, still more preferably 60 to 80% by weight, and particularly preferably 60 to 70% by weight. When the content of the above cyclic compound in the radiation-sensitive composition of the present embodiment is within the above range, high resolution is obtained and line edge roughness becomes small.

The radiation-sensitive composition of the present embodiment preferably contains one or more acid generating agents (C) generating an acid directly or indirectly by irradiation of any radiation selected from visible light, ultraviolet, excimer laser, electron beam, extreme ultraviolet (EUV), X-ray, and ion beam. The content of the acid generating agent (C) is preferably 0.001 to 49% by weight of the total weight of the solid component, more preferably 1 to 40% by weight, still more preferably 3 to 30% by weight, and particularly preferably 10 to 25% by weight. When the content of the acid generating agent (C) in the radiation-sensitive composition of the present embodiment is within the above range, a pattern profile with high sensitivity and low edge roughness is obtained. In the present embodiment, the acid generation method is not limited as long as an acid is generated within a system. By using excimer laser instead of ultraviolet such as g-ray and i-ray, finer processing is possible, and also by using electron beam, extreme ultraviolet, X-ray or ion beam as a high energy ray, further finer processing is possible.

The acid generating agent (C) is preferably at least one kind selected from the group consisting of compounds represented by the following formulae (7-1) to (7-8):

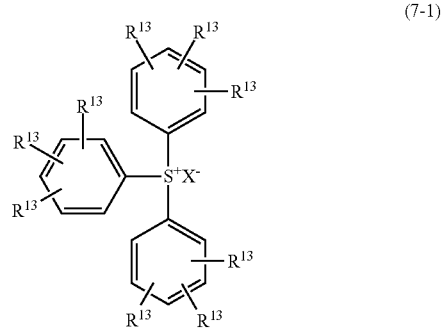

(7-1)

In the formula (7-1), $R^{13}$ may be the same or different, and are each independently a hydrogen atom, a linear, branched or cyclic alkyl group, a linear, branched or cyclic alkoxy group, a hydroxyl group, or a halogen atom; $X^-$ is an alkyl group, an aryl group, a sulfonic acid ion having a halogen substituted alkyl group or a halogen substituted aryl group, or a halide ion.

The compound represented by the above formula (7-1) is preferably at least one kind selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium-p-toluenesulfonate, triphenylsulfonium benzenesulfonate, diphenyl-2,4,6-trimethylphenyl-p-toluenesulfonate, diphenyl-2,4,6-trimethylphenylsulfonium-2-trifluoromethylbenzenesulfonate, diphenyl-2,4,6-trimethylphenylsulfonium-4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium-p-toluenesulfonate, triphenylsulfonium-10-camphorsulfonate, diphenyl-4-hydroxyphenylsulfonium-10-camphorsulfonate, and cyclo(1,3-perfluoropropanedisulfone)imidate.

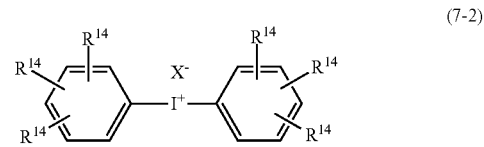

(7-2)

In the formula (7-2), $R^{14}$ may be the same or different, and each independently represents a hydrogen atom, a linear, branched or cyclic alkyl group, a linear, branched or cyclic alkoxy group, a hydroxyl group, or a halogen atom. $X^-$ is the same as above.

The compound represented by the above formula (7-2) is preferably at least one kind selected from the group consisting of bis(4-t-butylphenyl)iodonium trifluoromethanesulfonate, bis(4-t-butylphenyl)iodonium nonafluoro-n-butanesulfonate, bis(4-t-butylphenyl) iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethylbenzenesulfonate, bis(4-t-butylphenyl)iodonium-4-trifluoromethylbenzenesulfonate, bis(4-t-butylphenyl)iodonium-2,4-difluorobenzenesulfonate, bis(4-t-butylphenyl)iodonium hexafluorobenzenesulfonate, bis(4-t-butylphenyl)iodonium-10-camphorsulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium-10-camphorsulfonate, diphenyliodonium-2-trifluoromethylbenzenesulfonate, diphenyliodonium-4-trifluoromethylbenzenesulfonate, diphenyliodonium-2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium-p-toluenesulfonate, di(4-trifluoromethylphenyl)iodonium benzenesulfonate, and di(4-trifluoromethylphenyl)iodonium-10-camphersulfonate.

(7-3)

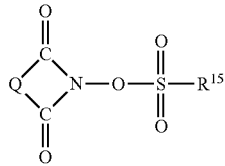

In the formula (7-3), Q is an alkylene group, an arylene group, or an alkoxylene group, and $R^{15}$ is an alkyl group, an aryl group, a halogen substituted alkyl group, or a halogen substituted aryl group.

The compound represented by the above formula (7-3) is preferably at least one kind selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-en-2,3-dicarboxyimide, N-(trifluoromethylsulfonyloxy)naphthylimide, N-(10-camphorsulfonyloxy)succinimide, N-(10-camphorsulfonyloxy)phthalimide, N-(10-camphorsulfonyloxy)diphenylmaleimide, N-(10-camphorsulfonyloxy)bicyclo[2.2.1]hept-5-en-2,3-dicarboxyimide, N-(10-camphorsulfonyloxy)naphthylimide, N-(n-octanesulfonyloxy)bicyclo[2.2.1]hept-5-en-2,3-dicarboxyimide, N-(n-octanesulfonyloxy)naphthylimide, N-(p-toluenesulfonyloxy)bicyclo[2.2.1]hept-5-en-2,3-dicarboxyimide, N-(p-toluenesulfonyloxy)naphthylimide, N-(2-trifluoromethylbenzenesulfonyloxy)bicyclo[2.2.1]hept-5-en-2,3-dicarboxyimide, N-(2-trifluoromethylbenzenesulfonyloxy)naphthylimide, N-(4-trifluoromethylbenzenesulfonyloxy)bicyclo[2.2.1]hept-5-en-2,3-dicarboxyimide, N-(4-trifluoromethylbenzenesulfonyloxy)naphthylimide, N-(perfluorobenzenesulfonyloxy)bicyclo[2.2.1]hept-5-en-2,3-dicarboxyimide, N-(perfluorobenzenesulfonyloxy)naphthylimide, N-(1-naphthalenesulfonyloxy)bicyclo[2.2.1]hept-5-en-2,3-dicarboxyimide, N-(1-naphthalenesulfonyloxy)naphthylimide, N-(nonafluoro-n-butanesulfonyloxy)bicyclo[2.2.1]hept-5-en-2,3-dicarboxyimide, N-(nonafluoro-n-butanesulfonyloxy)naphthylimide, N-(perfluoro-n-octanesulfonyloxy)bicyclo[2.2.1]hept-5-en-2,3-dicarboxyimide, and N-(perfluoro-n-octanesulfonyloxy)naphthylimide.

(7-4)

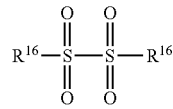

In the formula (7-4), $R^{16}$ may be the same or different, and are each independently an optionally substituted linear, branched or cyclic alkyl group, an optionally substituted aryl group, an optionally substituted heteroaryl group, or an optionally substituted aralkyl group.

The compound represented by the above formula (7-4) is preferably at least one kind selected from the group consisting of diphenyldisulfone, di(4-methylphenyl)disulfone, dinaphthyldisulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone, and di(4-trifluoromethylphenyl)disulfone.

(7-5)

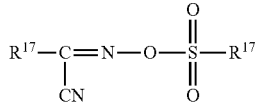

In the formula (7-5), $R^{17}$ may be the same or different, and are each independently an optionally substituted linear, branched or cyclic alkyl group, an optionally substituted aryl group, an optionally substituted heteroaryl group, or an optionally substituted aralkyl group.

The compound represented by the above formula (7-5) is preferably at least one kind selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

(7-6)

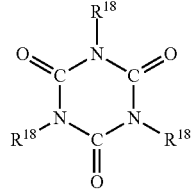

In the formula (7-6), $R^{18}$ may be the same or different, and are each independently a halogenated alkyl group having one or more chlorine atoms and one or more bromine atoms. The number of carbon atoms of the halogenated alkyl group is preferably 1 to 5.

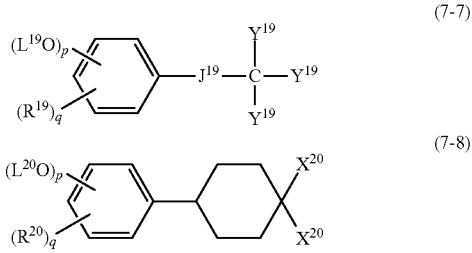

(7-7)

(7-8)

In the formulae (7-7) and (7-8), $R^{19}$ and $R^{20}$ are each independently an alkyl group having 1 to 3 carbon atoms such as a methyl group, an ethyl group, an n-propyl group, and an isopropyl group; a cycloalkyl group such as a cyclopentyl group and a cyclohexyl group; an alkoxyl group having 1 to 3 carbon atoms such as a methoxy group, an ethoxy group, and a propoxy group; or an aryl group such as a phenyl group, a toluoyl group, and a naphthyl group, and preferably an aryl group having 6 to 10 carbon atoms. $L^{19}$ and $L^{20}$ are each independently an organic group having a 1,2-naphthoquinonediazide group. Specifically, preferable examples of the organic group having a 1,2-naphthoquinonediazide group include a 1,2-quinonediazidesulfonyl group such as a 1,2-naphthoquinonediazide-4-sulfonyl group, a 1,2-naphthoquinonediazide-5-sulfonyl group, and a 1,2-naphthoquinonediazide-6-sulfonyl group. Particularly, a 1,2-naphthoquinonediazide-4-sulfonyl group and a 1,2-naphthoquinonediazide-5-sulfonyl group are preferable. p is an integer of 1 to 3; q is an integer of 0 to 4; and $1 \leq p+q \leq 5$. $J^{19}$ is a single bond, a polymethylene group having 1 to 4 carbon atoms, a cycloalkylene group, a phenylene group, a group represented by the following formula (7-7-1), a carbonyl group, an ester group, an amide group, or an ether group. $Y^{19}$ is a hydrogen atom, an alkyl group, or an aryl group, and $X^{20}$ are each independently a group represented by the following formula (7-8-1):

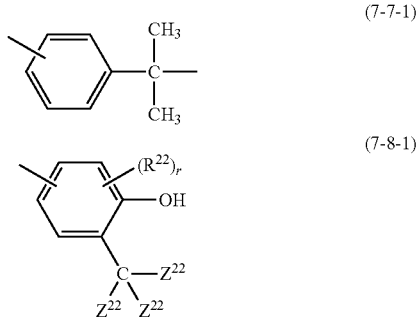

(7-7-1)

(7-8-1)

In the formula (7-8-1), $Z^{22}$ are each independently an alkyl group, a cycloalkyl group, or an aryl group; $R^{22}$ is an alkyl group, a cycloalkyl group, or an alkoxyl group; and r is an integer of 0 to 3.

Examples of the other acid generating agent include, but not particularly limited to, bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl) diazomethane, bis(n-propylsulfonyl)diazomethane, bis (cyclohexylsulfonyl)diazomethane, bis(isopropylsulfonyl) diazomethane, 1,3-bis (cyclohexylsulfonylazomethylsulfonyl)propane, 1,4-bis (phenylsulfonylazomethylsulfonyl)butane, 1,6-bis (phenylsulfonylazomethylsulfonyl)hexane, and 1,10-bis (cyclohexylsulfonylazomethylsulfonyl)decane; and halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine, and tris(2,3-dibromopropyl)isocyanurate.

Among the above acid generating agents, an acid generating agent having an aromatic ring is preferable, and an acid generating agent represented by the formula (7-1) or (7-2) is more preferable. An acid generating agent having a sulfonate ion wherein $X^-$ of the formula (7-1) or (7-2) has an aryl group or a halogen-substituted aryl group is still more preferable; an acid generating agent having a sulfonate ion having an aryl group is particularly preferable; and diphenyltrimethylphenylsulfonium-p-toluenesulfonate, triphenylsulfonium-p-toluenesulfonate, triphenylsulfonium trifluoromethanesulfonate, and triphenylsulfonium nonafluoromethanesulfonate are particularly preferable. By using the acid generating agent, LER can be further reduced.

The above acid generating agent (C) can be used alone or in combination of two or more kinds.

The radiation-sensitive composition of the present embodiment preferably contains one or more acid crosslinking agents (G). The acid crosslinking agent (G) is a compound capable of intramolecular or intermolecular crosslinking the cyclic compound described above in the presence of the acid generated from the acid generating agent (C). Examples of such an acid crosslinking agent (G) include a compound having one or more groups (hereinafter, referred to as "crosslinkable group") capable of crosslinking the cyclic compound of the formula (1).

Specific examples of such a crosslinkable group include, but not particularly limited to, (i) a hydroxyalkyl group such as a hydroxy (C1-C6 alkyl group), a C1-C6 alkoxy (C1-C6 alkyl group), and an acetoxy (C1-C6 alkyl group), or a group derived therefrom; (ii) a carbonyl group such as a formyl group and a carboxy (C1-C6 alkyl group), or a group derived therefrom; (iii) a nitrogenous group-containing group such as a dimethylaminomethyl group, a diethylaminomethyl group, a dimethylolaminomethyl group, a diethylolaminomethyl group, and a morpholinomethyl group; (iv) a glycidyl group-containing group such as a glycidyl ether group, a glycidyl ester group, and a glycidylamino group; (v) a group derived from an aromatic group such as a C1-C6 allyloxy (C1-C6 alkyl group) and a C1-C6 aralkyloxy (C1-C6 alkyl group) such as a benzyloxymethyl group and a benzoyloxymethyl group; and (vi) a polymerizable multiple bond-containing group such as a vinyl group and a isopropenyl group. As the crosslinkable group of the acid crosslinking agent (G) used in the present embodiment, a hydroxyalkyl group and an alkoxyalkyl group or the like are preferable, and an alkoxymethyl group is particularly preferable.

Examples of the acid crosslinking agent (G) having the above crosslinkable group include, but not particularly limited to, (i) a methylol group-containing compound such as a methylol group-containing melamine compound, a methylol group-containing benzoguanamine compound, a methylol group-containing urea compound, a methylol group-containing glycoluryl compound, and a methylol group-containing phenolic compound; (ii) an alkoxyalkyl group-containing compound such as an alkoxyalkyl group-containing melamine compound, an alkoxyalkyl group-containing benzoguanamine compound, an alkoxyalkyl group-containing urea compound, an alkoxyalkyl group-containing glycoluryl compound, and an alkoxyalkyl group-containing phenolic compound; (iii) a carboxymethyl group-containing compound such as a carboxymethyl group-containing melamine compound, a carboxymethyl group-containing benzoguanamine compound, a carboxymethyl group-containing urea compound, a carboxymethyl group-containing glycoluryl compound, and a carboxymethyl group-containing phenolic compound; (iv) an epoxy compound such as a bisphenol A based epoxy compound, a bisphenol F based epoxy compound, a bisphenol S based epoxy compound, a novolac resin based epoxy compound, a resol resin based epoxy compound, and a poly(hydroxystyrene) based epoxy compound.

As the acid crosslinking agent (G), a compound having a phenolic hydroxyl group, and a compound or resin where the above crosslinkable group is introduced into an acid functional group in an alkali soluble resin to impart crosslinkability can be further used. The introduction rate of the crosslinkable group in that case is adjusted to be normally 5 to 100 mol %, preferably 10 to 60 mol %, and more preferably 15 to 40 mol % based on the total acid functional groups in the compound having a phenolic hydroxyl group, and the alkali soluble resin. By having the introduction rate of the crosslinkable group within the above range, the crosslinking reaction sufficiently occurs, and a decrease in the film remaining rate, and swelling phenomena and meandering or the like of a pattern can be avoided, which is preferable.

In the radiation-sensitive composition of the present embodiment, as the acid crosslinking agent (G), an alkoxyalkylated urea compound or resin thereof, or an alkoxyalkylated glycoluryl compound or resin thereof is preferable. Particularly preferable examples of the acid crosslinking agent (G) include compounds represented by the following formulae (8-1) to (8-3) and an alkoxymethylated melamine compound (acid crosslinking agent (G1)).

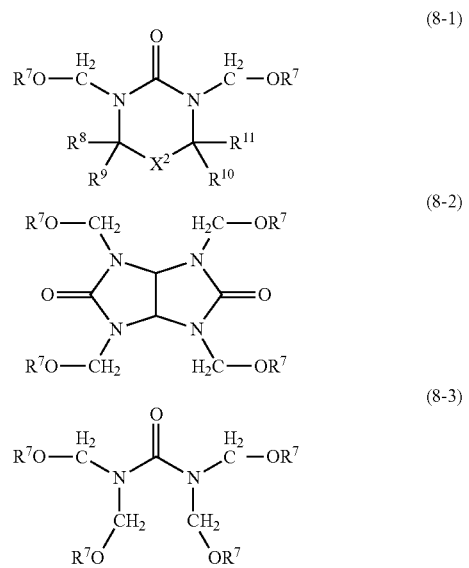

In the above formulae (8-1) to (8-3), $R^7$ each independently represents a hydrogen atom, an alkyl group, or an acyl group; $R^8$ to $R^{11}$ each independently represents a hydrogen atom, a hydroxyl group, an alkyl group, or an alkoxyl group; and $X^2$ represents a single bond, a methylene group, or an oxygen atom.

The number of carbon atoms of the alkyl group represented by $R^7$ is preferably 1 to 6, and more preferably 1 to 3.

Examples thereof include a methyl group, an ethyl group, and a propyl group. The number of carbon atoms of the acyl group represented by $R^7$ is preferably 2 to 6, and more preferably 2 to 4. Examples thereof include an acetyl group and a propyonyl group. The number of carbon atoms of the alkyl group represented by $R^8$ to $R^{11}$ is preferably 1 to 6, and more preferably 1 to 3. Examples thereof include a methyl group, an ethyl group, and a propyl group. The number of carbon atoms of the alkoxy group represented by $R^8$ to $R^{11}$ is preferably 1 to 6, and more preferably 1 to 3. Examples thereof include a methoxy group, an ethoxy group, and a propoxy group. $X^2$ is preferably a single bond or a methylene group. $R^7$ to $R^{11}$ and $X^2$ may be substituted with an alkyl group such as a methyl group and an ethyl group, an alkoxy group such as a methoxy group and an ethoxy group, a hydroxyl group, and a halogen atom or the like. A plurality of $R^7$ and $R^8$ to $R^{11}$ may be each the same or different.

Specific examples of the compound represented by the formula (8-1) include, but not particularly limited to, compounds shown below:

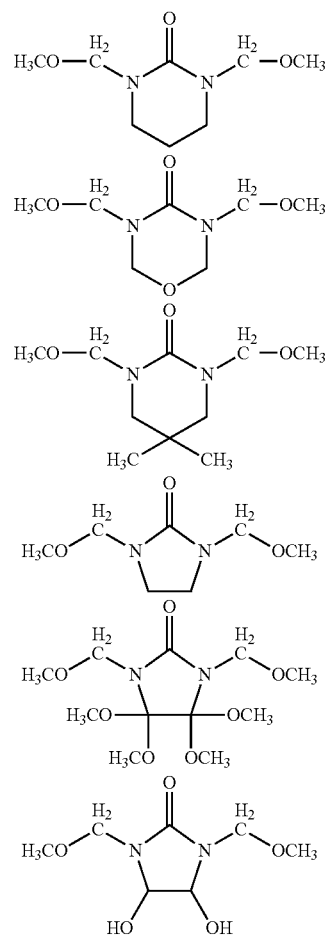

Specific examples of the compound represented by the formula (8-2) include, but not particularly limited to, N,N,N,N-tetra(methoxymethyl)glycoluryl, N,N,N,N-tetra(ethoxymethyl)glycoluryl, N,N,N,N-tetra(n-propoxymethyl)glycoluryl, N,N,N,N-tetra(isopropoxymethyl)glycoluryl, N,N,N,N-tetra(n-butoxymethyl)glycoluryl, and N,N,N,N-tetra(t-butoxymethyl)glycoluryl. Among them, particularly, N,N,N,N-tetra(methoxymethyl)glycoluryl is preferable.

Specific examples of the compound represented by the formula (8-3) include, but not particularly limited to, compounds shown below:

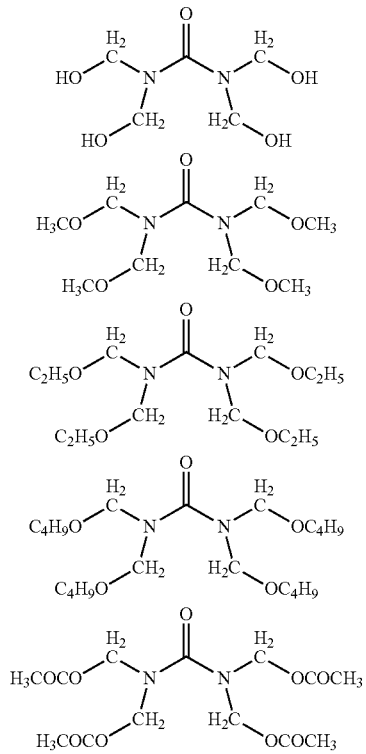

Specific examples of the alkoxymethylated melamine compound include N,N,N,N,N,N-hexa(methoxymethyl) melamine, N,N,N,N,N,N-hexa(ethoxymethyl)melamine, N,N,N,N,N,N-hexa(n-propoxymethyl)melamine, N,N,N,N, N,N-hexa(isopropoxymethyl)melamine, N,N,N,N,N,N-hexa (n-butoxymethyl)melamine, and N,N,N,N,N,N-hexa(t-butoxymethyl)melamine. Among them, particularly, N,N,N,N, N,N-hexa(methoxymethyl)melamine is preferable.

The above acid crosslinking agent (G1) can be obtained by, for example, conducting a condensation reaction of a urea compound or a glycoluryl compound with formalin to introduce an methylol group, etherifying the product with lower alcohols such as methyl alcohol, ethyl alcohol, propyl alcohol, and butyl alcohol, and then cooling the reaction solution to collect a precipitated compound or resin thereof. The above acid crosslinking agent (G1) can be obtained as a commercially available product such as CYMEL (trade name, manufactured by MT AquaPolymer) and NIKALAC (manufactured by Sanwa Chemical).

Other particularly preferable examples of the acid crosslinking agent (G) include a phenol derivative having 1 to 6 benzene rings within a molecule and two or more hydroxyalkyl groups and/or alkoxyalkyl groups within the entire molecule, the hydroxyalkyl groups and/or alkoxyalkyl groups being bonded to any of the above benzene rings (acid crosslinking agent (G2)). Preferable examples thereof include a phenol derivative having a molecular weight of 1500 or less, 1 to 6 benzene rings and a total of two or more hydroxyalkyl groups and/or alkoxyalkyl groups within a molecule, the hydroxyalkyl groups and/or alkoxyalkyl groups being bonded to any one of the above benzene rings, or a plurality of benzene rings.

As the hydroxyalkyl group bonded to a benzene ring, the one having 1 to 6 carbon atoms such as a hydroxymethyl group, a 2-hydroxyethyl group, and a 2-hydroxy-1-propyl group is preferable. As the alkoxyalkyl group bonded to a benzene ring, the one having 2 to 6 carbon atoms is preferable. Specifically, a methoxymethyl group, an ethoxymethyl group, an n-propoxymethyl group, an isopropoxymethyl group, an n-butoxymethyl group, an isobutoxymethyl group, a sec-butoxymethyl group, a t-butoxymethyl group, a 2-methoxyethyl group, or a 2-methoxy-1-propyl group is preferable.

Among these phenol derivatives, particularly preferable ones are shown below:

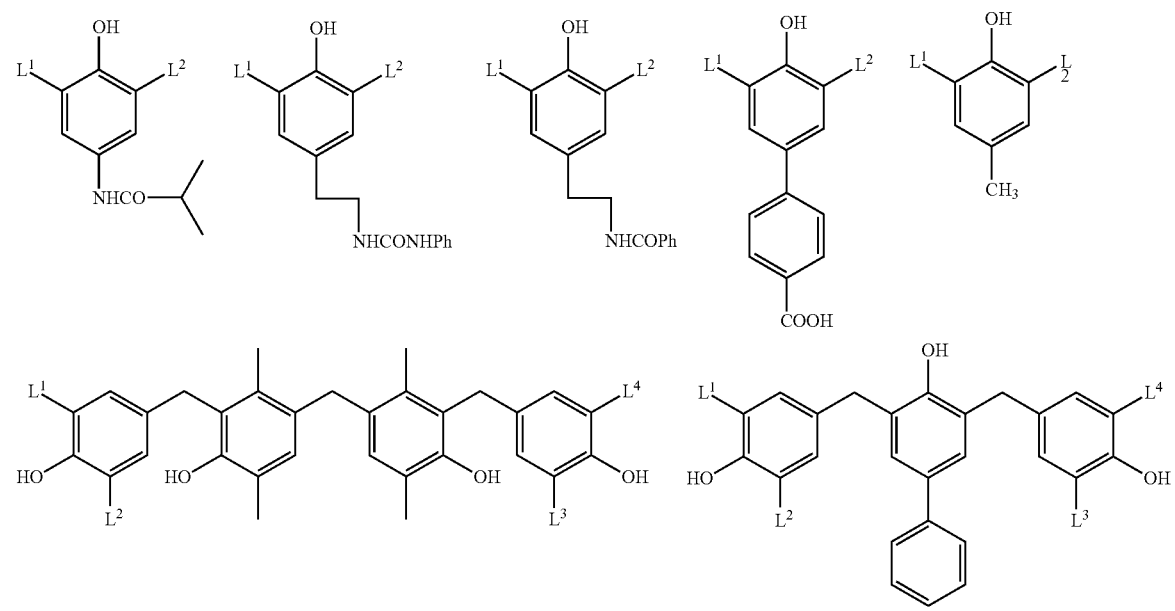

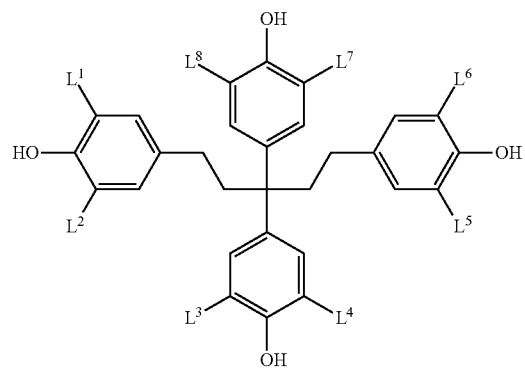
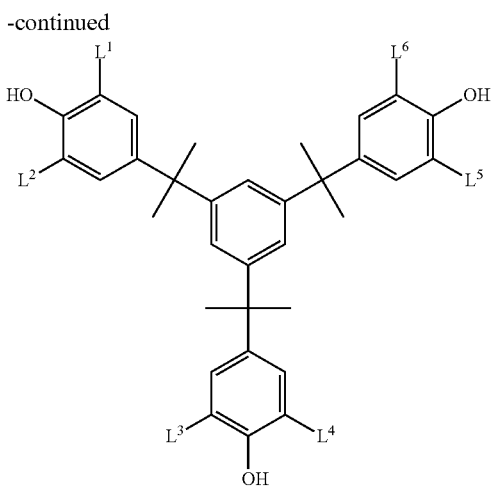
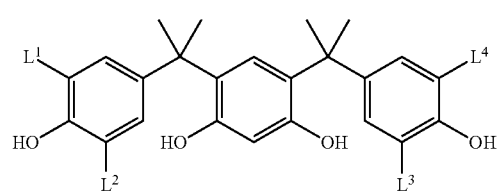
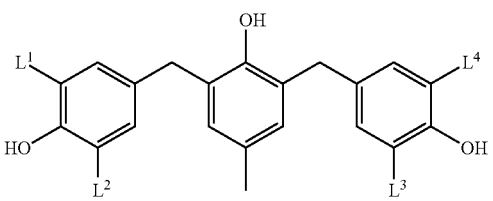
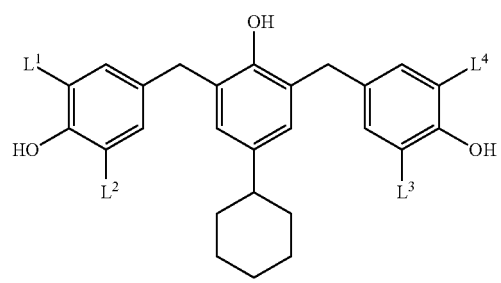
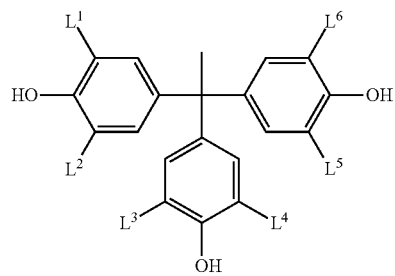
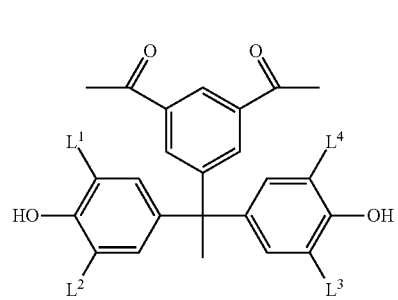
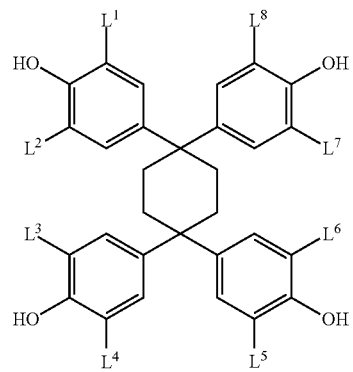
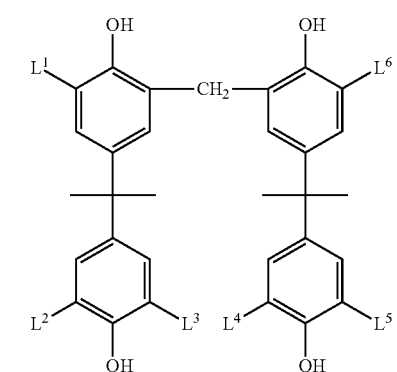
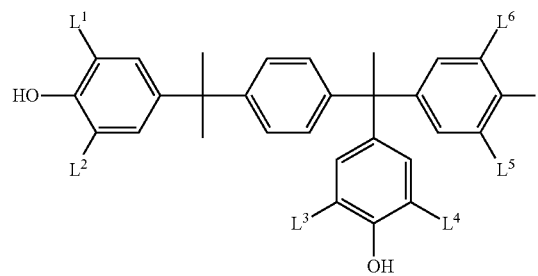
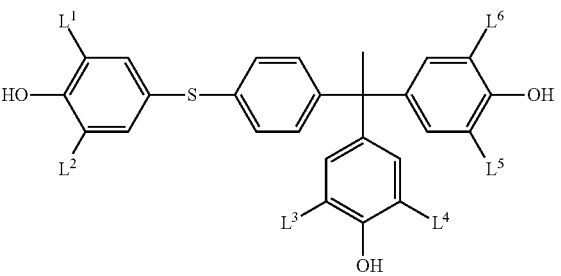

-continued

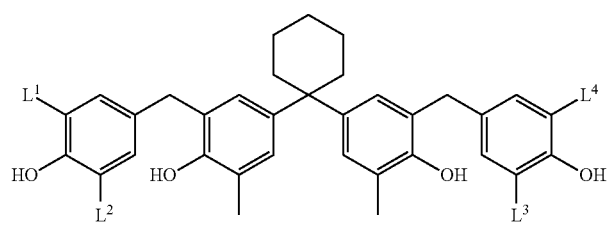
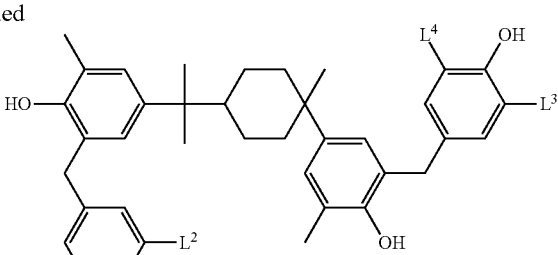
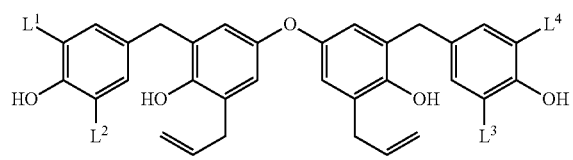
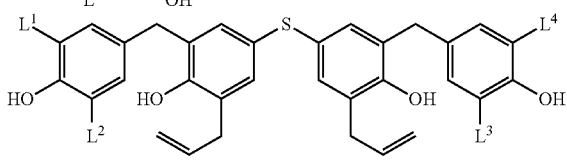
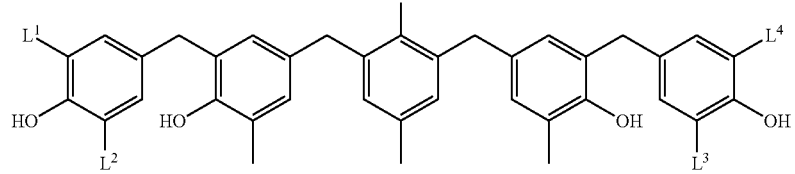
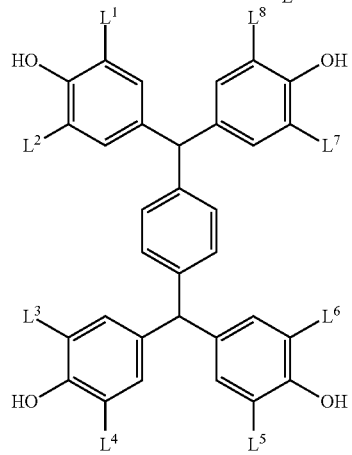

In the above formulae, $L^1$ to $L^8$ may be the same or different, and each independently represents a hydroxymethyl group, a methoxymethyl group, or an ethoxymethyl group. A phenol derivative having a hydroxymethyl group can be obtained by reacting the corresponding phenolic compound having no hydroxymethyl group (a compound where $L^1$ to $L^8$ in the above formulae are a hydrogen atom) with formaldehyde in the presence of a basic catalyst. In this case, in order to prevent resinification and gelation, the reaction temperature is preferably 60° C. or less. Specifically, it can be synthesized by methods described in Japanese Patent Application Laid-Open Nos. 6-282067 and 7-64285 or the like.

A phenol derivative having an alkoxymethyl group can be obtained by reacting the corresponding phenol derivative having a hydroxymethyl group with an alcohol in the presence of an acid catalyst. In this case, in order to prevent resinification and gelation, the reaction temperature is preferably 100° C. or less. Specifically, it can be synthesized by methods described in EP632003A1 or the like.

While the phenol derivative having a hydroxymethyl group and/or an alkoxymethyl group thus synthesized is preferable in terms of stability upon storage, the phenol derivative having an alkoxymethyl group is particularly preferable in terms of stability upon storage. The acid crosslinking agent (G2) may be used alone, or may be used in combination of two or more kinds.

Other particularly preferable examples of the acid crosslinking agent (G) include a compound having at least one α-hydroxyisopropyl group (acid crosslinking agent (G3)). The compound is not particularly limited in the structure, as long as it has an α-hydroxyisopropyl group. A hydrogen atom of a hydroxyl group in the above α-hydroxyisopropyl group may be substituted with one or more acid dissociation groups (R—COO— group, R—SO$_2$— group or the like, wherein R represents a substituent group selected from the group consisting of a linear hydrocarbon group having 1 to 12 carbon atoms, a cyclic hydrocarbon group having 3 to 12 carbon atoms, an alkoxy group having 1 to 12 carbon atoms, a 1-branched alkyl group having 3 to 12 carbon atoms, and an aromatic hydrocarbon group having 6 to 12 carbon atoms). Examples of a compound having the above α-hydroxyisopropyl group include, but not particularly limited to, one kind or two kinds or more of a substituted or non-substituted aromatic based compound, a diphenyl compound, a naphthalene compound, a furan compound or the like containing at least one α-hydroxyisopropyl group. Specific examples thereof include, but not particularly limited to, a compound represented by the following general formula (9-1) (hereinafter, referred to as "benzene based compound (1)"), a compound represented by the following general formula (9-2) (hereinafter, referred to as "diphenyl based compound (2)"), a compound represented by the following general formula (9-3) (hereinafter, referred to as "naphthalene based compound (3)"), and a compound represented by the following general formula (9-4) (hereinafter, referred to as "furan based compound (4)").

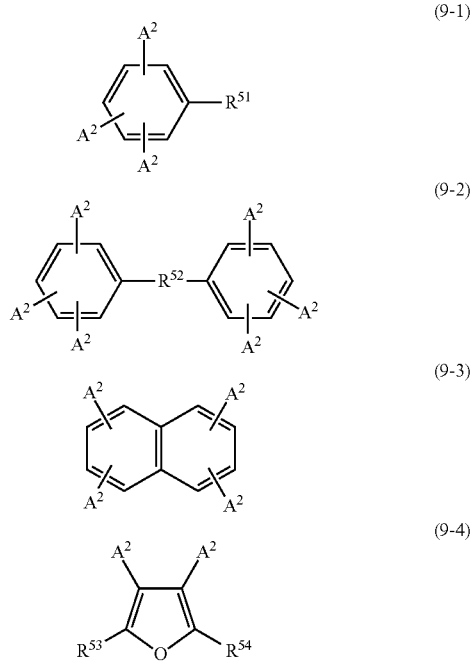

(9-1)

(9-2)

(9-3)

(9-4)

In the above general formulae (9-1) to (9-4), each $A^2$ independently represents an α-hydroxyisopropyl group or a hydrogen atom, and at least one of $A^2$ is an α-hydroxyisopropyl group. In the general formula (9-1), $R^{51}$ represents a hydrogen atom, a hydroxyl group, a linear or branched alkylcarbonyl group having 2 to 6 carbon atoms, or a linear or branched alkoxycarbonyl group having 2 to 6 carbon atoms. Furthermore, in the general formula (9-2), $R^{52}$ represents a single bond, a linear or branched alkylene group having 1 to 5 carbon atoms, —O—, —CO—, or —COO—. Also, in the general formula (9-4), $R^{53}$ and $R^{54}$ represent a hydrogen atom or a linear or branched alkyl group having 1 to 6 carbon atoms each independently.

Specific examples of the benzene based compound (1) include, but not particularly limited to, α-hydroxyisopropylbenzenes such as α-hydroxyisopropylbenzene, 1,3-bis(α-hydroxyisopropyl)benzene, 1,4-bis(α-hydroxyisopropyl)benzene, 1,2,4-tris(α-hydroxyisopropyl)benzene, and 1,3,5-tris(α-hydroxyisopropyl)benzene; α-hydroxyisopropylphenols such as 3-α-hydroxyisopropylphenol, 4-α-hydroxyisopropylphenol, 3,5-bis(α-hydroxyisopropyl)phenol, and 2,4,6-tris(α-hydroxyisopropyl)phenol; α-hydroxyisopropylphenyl alkyl ketones such as 3-α-hydroxyisopropylphenyl methyl ketone, 4-α-hydroxyisopropylphenyl methyl ketone, 4-α-hydroxyisopropylphenyl ethyl ketone, 4-α-hydroxyisopropylphenyl-n-propyl ketone, 4-α-hydroxyisopropylphenyl iso-propyl ketone, 4-α-hydroxyisopropylphenyl-n-butyl ketone, 4-α-hydroxyisopropylphenyl-t-butyl ketone, 4-α-hydroxyisopropylphenyl-n-pentyl ketone, 3,5-bis(α-hydroxyisopropyl)phenyl methyl ketone, 3,5-bis(α-hydroxyisopropyl)phenyl ethyl ketone, and 2,4,6-tris(α-hydroxyisopropyl)phenyl methyl ketone; alkyl 4-α-hydroxyisopropylbenzoates such as methyl 3-αhydroxyisopropylbenzoate, methyl 4-α-hydroxyisopropylbenzoate, ethyl 4-α-hydroxyisopropylbenzoate, n-propyl 4-α-hydroxyisopropylbenzoate, isopropyl 4-α-hydroxyisopropylbenzoate, n-butyl 4-α-hydroxyisopropylbenzoate, t-butyl 4-α-hydroxyisopropylbenzoate, n-pentyl 4-α-hydroxyisopropylbenzoate, methyl 3,5-bis(α-hydroxyisopropyl)benzoate, ethyl 3,5-bis(α-hydroxyisopropyl)benzoate, and methyl 2,4,6-tris(α-hydroxyisopropyl)benzoate.

Specific examples of the above diphenyl based compound (2) include, but not particularly limited to, α-hydroxyisopropylbiphenyls such as 3-α-hydroxyisopropylbiphenyl, 4-α-hydroxyisopropylbiphenyl, 3,5-bis(α-hydroxyisopropyl)biphenyl, 3,3'-bis(α-hydroxyisopropyl)biphenyl, 3,4'-bis(α-hydroxyisopropyl)biphenyl, 4,4'-bis(α-hydroxyisopropyl)biphenyl, 2,4,6-tris(α-hydroxyisopropyl)biphenyl, 3,3',5-tris(α-hydroxyisopropyl)biphenyl, 3,4',5-tris(α-hydroxyisopropyl)biphenyl, 2,3',4,6,-tetrakis(α-hydroxyisopropyl)biphenyl, 2,4,4',6,-tetrakis(α-hydroxyisopropyl)biphenyl, 3,3',5,5'-tetrakis(α-hydroxyisopropyl)biphenyl, 2,3',4,5',6-pentakis(α-hydroxyisopropyl)biphenyl, and 2,2',4,4',6,6'-hexakis(α-hydroxyisopropyl)biphenyl;

α-hydroxyisopropyldiphenylalkanes such as 3-α-hydroxyisopropyldiphenylmethane, 4-α-hydroxyisopropyldiphenylmethane, 1-(4-α-hydroxyisopropylphenyl)-2-phenylethane, 1-(4-α-hydroxyisopropylphenyl)-2-phenylpropane, 2-(4-α-hydroxyisopropylphenyl)-2-phenylpropane, 1-(4-α-hydroxyisopropylphenyl)-3-phenylpropane, 1-(4-α-hydroxyisopropylphenyl)-4-phenylbutane, 1-(4-α-hydroxyisopropylphenyl)-5-phenylpentane, 3,5-bis(α-hydroxyisopropyldiphenylmethane, 3,3'-bis(α-hydroxyisopropyl)diphenylmethane, 3,4'-bis(α-hydroxyisopropyl)diphenylmethane, 4,4'-bis(α-hydroxyisopropyl)diphenylmethane, 1,2-bis(4-α-hydroxyisopropylphenyl)ethane, 1,2-bis(4-α-hydroxypropylphenyl)propane, 2,2-bis(4-α-hydroxypropylphenyl)propane, 1,3-bis(4-α-hydroxypropylphenyl)propane, 2,4,6-tris(α-hydroxyisopropyl)diphenylmethane, 3,3',5-tris(α-hydroxyisopropyl)diphenylmethane, 3,4',5-tris(α-hydroxyisopropyl)diphenylmethane, 2,3',4,6-tetrakis(α-hydroxyisopropyl)diphenylmethane, 2,4,4',6-tetrakis(α-hydroxyisopropyl)diphenylmethane, 3,3',5,5'-tetrakis(α-hydroxyisopropyl)diphenylmethane, 2,3',4,5',6-pentakis(α-hydroxyisopropyl)diphenylmethane, and 2,2',4,4',6,6'-hexakis(α-hydroxyisopropyl)diphenylmethane;

α-hydroxyisopropyldiphenyl ethers such as 3-α-hydroxyisopropyldiphenyl ether, 4-α-hydroxyisopropyldiphenyl ether, 3,5-bis(α-hydroxyisopropyl)diphenyl ether, 3,3'-bis(α-hydroxyisopropyl)diphenyl ether, 3,4'-bis(α-hydroxyisopropyl)diphenyl ether, 4,4'-bis(α-hydroxyisopropyl)diphenyl ether, 2,4,6-tris(α-hydroxyisopropyl)diphenyl ether, 3,3',5-tris(α-hydroxyisopropyl)diphenyl ether, 3,4',5-tris(α-hydroxyisopropyl)diphenyl ether, 2,3',4,6-tetrakis(α-hydroxyisopropyl)diphenyl ether, 2,4,4',6-tetrakis(α-hydroxyisopropyl)diphenyl ether, 3,3',5,5'-tetrakis(α-hydroxyisopropyl)diphenyl ether, 2,3',4,5',6-pentakis(α-hydroxyisopropyl)diphenyl ether, and 2,2',4,4',6,6'-hexakis(α-hydroxyisopropyl)diphenyl ether;

α-hydroxyisopropyldiphenyl ketones such as 3-α-hydroxyisopropyldiphenyl ketone, 4-α-hydroxyisopropyldiphenyl ketone, 3,5-bis(α-hydroxyisopropyl)diphenyl ketone, 3,3'-bis(α-hydroxyisopropyl)diphenyl ketone, 3,4'-bis(α-hydroxyisopropyl)diphenyl ketone, 4,4'-bis(α-hydroxyisopropyl)diphenyl ketone, 2,4,6-tris(α-hydroxyisopropyl)diphenyl ketone, 3,3',5-tris(α-hydroxyisopropyl)diphenyl ketone, 3,4',5-tris(α-hydroxyisopropyl)diphenyl ketone, 2,3',4,6-tetrakis(α-hydroxyisopropyl)diphenyl ketone, 2,4,4',6-tetrakis(α-hydroxyisopropyl)diphenyl ketone, 3,3',5,5'-tetrakis(α-hydroxyisopropyl)diphenyl ketone, 2,3',4,5',6-pentakis(α-hydroxyisopropyl)diphenyl ketone, and 2,2',4,4',6,6'-hexakis(α-hydroxyisopropyl)diphenyl ketone; phenyl α-hydroxyisopropylbenzoates such as phenyl 3-α-hydroxyisopropylbenzoate, phenyl 4-α-hydroxyisopropylbenzoate, 3-α-hydroxyisopropylphenyl benzoate, 4-α-hydroxyisopropylphenyl benzoate, phenyl 3,5-bis(α-hydroxyisopropyl)benzoate, 3-α-hydroxyisopropylphenyl 3-α-hydroxyisopropylbenzoate, 4-α-hydroxyisopropylphenyl 3-α-hydroxyisopropylbenzoate, 3-α-hydroxyisopropylphenyl 4-α-hydroxyisopropylbenzoate, 4-α-hydroxyisopropylphenyl 4-α-hydroxyisopropylbenzoate, 3,5-bis(α-hydroxyisopropyl)phenyl benzoate, phenyl 2,4,6-tris(α-hydroxyisopropyl)benzoate, 3-α-hydroxyisopropylphenyl 3,5-bis(α-hydroxyisopropyl)benzoate, 4-α-hydroxyisopropylphenyl 3,5-bis(α-hydroxyisopropyl)benzoate, 3,5-bis(α-hydroxyisopropyl)phenyl 3-α-hydroxyisopropylbenzoate, 3,5-bis(α-hydroxyisopropyl)phenyl 4-α-hydroxyisopropylbenzoate, 2,4,6-tris(α-hydroxyisopropyl)phenyl benzoate, 3-α-hydroxyisopropylphenyl 2,4,6-tris(α-hydroxyisopropyl)benzoate, 4-α-hydroxyisopropylphenyl 2,4,6-tris(α-hydroxyisopropyl)benzoate, 3,5-bis(α-hydroxyisopropyl) phenyl 3,5-bis(α-hydroxyisopropyl)benzoate, 2,4,6-tris(α-hydroxyisopropyl)phenyl 3-α-hydroxyisopropylbenzoate, 2,4,6-tris(α-hydroxyisopropyl)phenyl 4-α-hydroxyisopropylbenzoate, 3,5-bis(α-hydroxyisopropyl)phenyl 2,4,6-tris(α-hydroxyisopropyl)benzoate, 2,4,6-tris(α-hydroxyisopropyl)phenyl 3,5-bis(α-hydroxyisopropyl)benzoate, and 2,4,6-tris(α-hydroxyisopropyl)phenyl 2,4,6-tris(α-hydroxyisopropyl)benzoate.

Furthermore, specific examples of the above naphthalene based compound (3) include, but not particularly limited to, 1-(α-hydroxyisopropyl)naphthalene, 2-(α-hydroxyisopropyl)naphthalene, 1,3-bis(α-hydroxyisopropyl)naphthalene, 1,4-bis(α-hydroxyisopropyl)naphthalene, 1,5-bis(α-hydroxyisopropyl)naphthalene, 1,6-bis(α-hydroxyisopropyl)naphthalene, 1,7-bis(α-hydroxyisopropyl)naphthalene, 2,6-bis(α-hydroxyisopropyl)naphthalene, 2,7-bis(α-hydroxyisopropyl)naphthalene, 1,3,5-tris(α-hydroxyisopropyl) naphthalene, 1,3,6-tris(α-hydroxyisopropyl)naphthalene, 1,3,7-tris(α-hydroxyisopropyl)naphthalene, 1,4,6-tris(α-hydroxyisopropyl)naphthalene, 1,4,7-tris(α-hydroxyisopropyl)naphthalene, and 1,3,5,7-tetrakis(α-hydroxyisopropyl) naphthalene.

Specific examples of the above furan based compound (4) include, but not particularly limited to, 3-(α-hydroxyisopropyl)furan, 2-methyl-3-(α-hydroxyisopropyl)furan, 2-methyl-4-(α-hydroxyisopropyl)furan, 2-ethyl-4-(α-hydroxyisopropyl)furan, 2-n-propyl-4-(α-hydroxyisopropyl)furan, 2-isopropyl-4-(α-hydroxyisopropyl)furan, 2-n-butyl-4-(α-hydroxyisopropyl)furan, 2-t-butyl-4-(α-hydroxyisopropyl) furan, 2-n-pentyl-4-(α-hydroxyisopropyl)furan, 2,5-dimethyl-3-(α-hydroxyisopropyl)furan, 2,5-diethyl-3-(α-hydroxyisopropyl)furan, 3,4-bis(α-hydroxyisopropyl)furan, 2,5-dimethyl-3,4-bis(α-hydroxyisopropyl)furan, and 2,5-diethyl-3,4-bis(α-hydroxyisopropyl)furan.

As the above acid crosslinking agent (G3), a compound having two or more free α-hydroxyisopropyl groups is preferable; the above benzene based compound (1) having two or more α-hydroxyisopropyl groups, the above diphenyl based compound (2) having two or more α-hydroxyisopropyl groups, and the above naphthalene based compound (3) having two or more α-hydroxyisopropyl groups are more preferable; and α-hydroxyisopropylbiphenyls having two or more α-hydroxyisopropyl groups and the above naphthalene based compound (3) having two or more α-hydroxyisopropyl groups are particularly preferable.

The above acid crosslinking agent (G3) can normally be obtained by a method for reacting an acetyl group-containing compound such as 1,3-diacetylbenzene with Grignard reagent such as $CH_3MgBr$ to methylate and then hydrolyzing, or a method for oxidizing an isopropyl group-containing compound such as 1,3-diisopropylbenzene with oxygen or the like to produce a peroxide and then reducing.

The content of the acid crosslinking agent (G) in the radiation-sensitive composition of the present embodiment is preferably 0.5 to 49% by weight of the total weight of the solid component, more preferably 0.5 to 40% by weight, still more preferably 1 to 30% by weight, and particularly preferably 2 to 20% by weight. When the content of the above acid crosslinking agent (G) in the radiation-sensitive composition of the present embodiment is 0.5% by weight or more, the inhibiting effect of the solubility of a resist film in an alkaline developing solution can be improved, and a decrease in the film remaining rate, and occurrence of swelling and meandering of a pattern can be inhibited, which is preferable. On the other hand, when the content of the above acid crosslinking agent (G) is 50% by weight or less, a decrease in heat resistance as a resist can be inhibited, which is preferable.

The blending ratio of at least one kind of compound selected from the above acid crosslinking agent (G1), acid crosslinking agent (G2), and acid crosslinking agent (G3) in the above acid crosslinking agent (G) is also not particularly limited, and can be within various ranges according to the kind of substrates or the like used upon forming a resist pattern.

In all acid crosslinking agent components, the contents of the above alkoxymethylated melamine compound and/or the compounds represented by (9-1) to (9-3) are 50 to 99% by weight, preferably 60 to 99% by weight, more preferably 70 to 98% by weight, and still more preferably 80 to 97% by weight. By having the contents of the alkoxymethylated melamine compound and/or the compounds represented by (9-1) to (9-3) of 50% by weight or more of all acid crosslinking agent components, the resolution of the radiation-sensitive composition of the present embodiment can be improved, which is preferable. By having the compounds of 99% by weight or less, the pattern cross section is likely to have a rectangular shape, which is preferable.

The radiation-sensitive composition of the present embodiment may further contain an acid diffusion controlling agent (E). The acid diffusion controlling agent (E) has a function of controlling diffusion of an acid generated from an acid generating agent by radiation irradiation in a resist film to inhibit any unpreferable chemical reaction in an unexposed region or the like. When the radiation-sensitive composition of the present embodiment contains such an acid diffusion controlling agent (E), the storage stability of the radiation-sensitive composition is improved. Also, along with the improvement of the resolution, the line width change of a resist pattern due to variation in the post exposure delay time before radiation irradiation and the post exposure delay time after radiation irradiation can be inhibited, and the composition has extremely excellent process stability. Examples of such an acid diffusion controlling agent (E) include, but not particularly limited to, a radiation degradable basic compound such as a nitrogen atom-containing basic compound, a basic sulfonium compound, and a basic iodonium compound. The acid diffusion controlling agent (E) can be used alone or in combination of two or more kinds.

Examples of the above acid diffusion controlling agent (E) include, but not particularly limited to, a nitrogen-containing organic compound, and a basic compound degradable by exposure. Examples of the above nitrogen-containing organic compound include a compound represented by the following general formula (10):

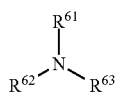
(10)

(hereinafter, referred to as a "nitrogen-containing compound (I)"), a diamino compound having two nitrogen atoms within the same molecule (hereinafter, referred to as a "nitrogen-containing compound (II)"), a polyamino compound or polymer having three or more nitrogen atoms (hereinafter, referred to as a "nitrogen-containing compound (III)"), an amide group-containing compound, a urea compound, and a nitrogen-containing heterocyclic compound. The acid diffusion controlling agent (E) may be used alone as one kind or may be used in combination of two or more kinds.

In the above general formula (10), $R^{61}$, $R^{62}$, and $R^{63}$ represent a hydrogen atom, a linear, branched or cyclic alkyl group, an aryl group, or an aralkyl group each independently. The above alkyl group, aryl group, or aralkyl group may be non-substituted or may be substituted with a hydroxyl group or the like. Herein, examples of the above linear, branched or cyclic alkyl group include the one having 1 to 15, and preferably 1 to 10 carbon atoms. Specific examples thereof include, but not particularly limited to, a methyl group, an ethyl group, an n-propyl group, an isopropyl group, an n-butyl group, an isobutyl group, a sec-butyl group, a t-butyl group, an n-pentyl group, a neopentyl group, an n-hexyl group, a texyl group, an n-heptyl group, an n-octyl group, an n-ethylhexyl group, an n-nonyl group, and an n-decyl group. Examples of the above aryl group include the one having 6 to 12 carbon atoms. Specific examples thereof include, but not particularly limited to, a phenyl group, a tolyl group, a xylyl group, a cumenyl group, and a 1-naphthyl group. Furthermore, examples of the above aralkyl group include, but not particularly limited to, the one having 7 to 19, and preferably 7 to 13 carbon atoms. Specific examples thereof include a benzyl group, an α-methylbenzyl group, a phenethyl group, and a naphthylmethyl group.

Specific examples of the above nitrogen-containing compound (I) include, but not particularly limited to, mono(cyclo)alkylamines such as n-hexylamine, n-heptylamine, n-octylamine, n-nonylamine, n-decylamine, n-dodecylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylm- ethylamine, and tricyclohexylamine; alkanolamines such as monoethanolamine, diethanolamine, and triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

Specific examples of the above nitrogen-containing compound (II) include, but not particularly limited to, ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

Specific examples of the above nitrogen-containing compound (III) include, but not particularly limited to, polymers of polyethyleneimine, polyarylamine, and N-(2-dimethylaminoethyl)acrylamide.

Specific examples of the above amide group-containing compound include, but not particularly limited to, formamide, N-methylformamide, N,N-dimethylformamide, acetamide, N-methylacetamide, N,N-dimethylacetamide, propioneamide, benzamide, pyrrolidone, and N-methylpyrrolidone.

Specific examples of the above urea compound include, but not particularly limited to, urea, methylurea, 1,1-dimethylurea, 1,3-dimethylurea, 1,1,3,3-tetramethylurea, 1,3-diphenylurea, and tri-n-butylthiourea.

Specific examples of the above nitrogen-containing heterocyclic compound include, but not particularly limited to, imidazoles such as imidazole, benzimidazole, 4-methylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, amide nicotinate, quinoline, 8-oxyquinoline, and acridine; and pyrazine, pyrazole, pyridazine, quinozaline, purine, pyrrolidine, piperidine, morpholine, 4-methylmorpholine, piperazine, 1,4-dimethylpiperazine, and 1,4-diazabicyclo[2.2.2]octane.

Examples of the above radiation degradable basic compound include, but not particularly limited to, a sulfonium compound represented by the following general formula (11-1):

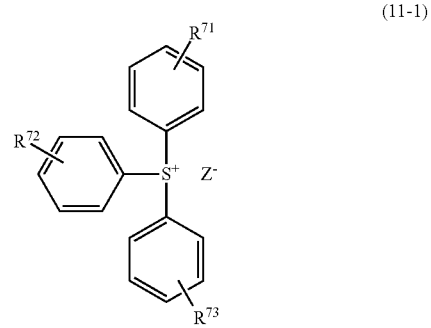
(11-1)

and an iodonium compound represented by the following general formula (11-2):

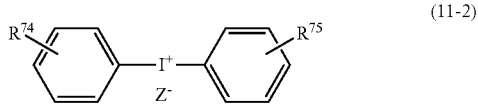

In the above general formulae (11-1) and (11-2), $R^{71}$, $R^{72}$, $R^{73}$, $R^{74}$, and $R^{75}$ represent a hydrogen atom, an alkyl group having 1 to 6 carbon atoms, an alkoxyl group having 1 to 6 carbon atoms, a hydroxyl group, or a halogen atom each independently. $Z^-$ represents $HO^-$, $R-COO^-$ (R represents an alkyl group having 1 to 6 carbon atoms, an aryl group having 6 to 11 carbon atoms, or an alkaryl group having 7 to 12 carbon atoms), or an anion represented by the following general formula (11-3):

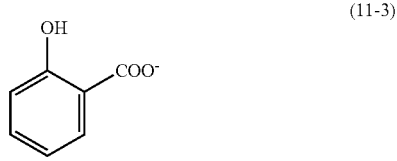

Specific examples of the above radiation degradable basic compound include, but not particularly limited to, triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl)iodonium hydroxide, bis(4-t-butylphenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, and 4-t-butylphenyl-4-hydroxyphenyliodonium salicylate.

The content of the acid diffusion controlling agent (E) in the radiation-sensitive composition of the present embodiment is preferably 0.001 to 49% by weight of the total weight of the solid component, more preferably 0.01 to 10% by weight, still more preferably 0.01 to 5% by weight, and particularly preferably 0.01 to 3% by weight. When the content of the acid diffusion controlling agent (E) in the radiation-sensitive composition of the present embodiment is within the above range, a decrease in resolution, and deterioration of the pattern shape and the dimension fidelity or the like can be prevented. Moreover, even though the post exposure delay time from electron beam irradiation to heating after radiation irradiation becomes longer, the shape of the pattern upper layer portion is not deteriorated. When the content of the acid diffusion controlling agent (E) in the radiation-sensitive composition of the present embodiment is 10% by weight or less, a decrease in sensitivity, and developability of the unexposed portion or the like can be prevented. By using such an acid diffusion controlling agent (E), the storage stability of a radiation-sensitive composition improves, also along with improvement of the resolution, the line width change of a resist pattern due to variation in the post exposure delay time before radiation irradiation and the post exposure delay time after radiation irradiation can be inhibited, and the composition has extremely excellent process stability.

To the radiation-sensitive composition of the present embodiment, within the range of not inhibiting the purpose of the present invention, if required, as the other component (F), one kind or two kinds or more of various additive agents such as a dissolution promoting agent, a dissolution controlling agent, a sensitizing agent, a surfactant and an organic carboxylic acid or an oxo acid of phosphor, or derivative thereof can be added.

(1) Dissolution Promoting Agent

A dissolution promoting agent is a component having a function of increasing the solubility of a cyclic compound such as described above in a developing solution to moderately increase the dissolution rate of the cyclic compound upon developing, when the solubility of the cyclic compound is too low. The low molecular weight dissolution promoting agent can be used, within the range of not deteriorating the effect of the present invention. Examples of the above dissolution promoting agent include, but not particularly limited to, a low molecular weight phenolic compound. Specific examples thereof include bisphenols and tris(hydroxyphenyl) methane. These dissolution promoting agents can be used alone or in mixture of two or more kinds. The content of the dissolution promoting agent in the radiation-sensitive composition of the present embodiment, which is arbitrarily adjusted according to the kind of cyclic compound to be used, is preferably 0 to 49% by weight of the total weight of the solid component, more preferably 0 to 5% by weight, still more preferably 0 to 1% by weight, and particularly preferably 0% by weight.

(2) Dissolution Controlling Agent

The dissolution controlling agent is a component having a function of controlling the solubility of the cyclic compound such as described above in a developing solution to moderately decrease the dissolution rate upon developing, when the solubility of the cyclic compound is too high. As such a dissolution controlling agent, the one which does not chemically change in steps such as calcination of resist coating, radiation irradiation, and development is preferable.

Examples of the dissolution controlling agent include, but not particularly limited to, aromatic hydrocarbons such as phenanthrene, anthracene, and acenaphthene; ketones such as acetophenone, benzophenone, and phenyl naphtyl ketone; and sulfones such as methyl phenyl sulfone, diphenyl sulfone, and dinaphthyl sulfone. These dissolution controlling agents can be used alone or in two or more kinds.

The content of the dissolution controlling agent in the radiation-sensitive composition of the present embodiment, which is arbitrarily adjusted according to the kind of cyclic compound to be used, is preferably 0 to 49% by weight of the total weight of the solid component, more preferably 0 to 5% by weight, still more preferably 0 to 1% by weight, and particularly preferably 0% by weight.

(3) Sensitizing Agent

The sensitizing agent is a component having a function of absorbing irradiated radiation energy, transmitting the energy to the acid generating agent (C), and thereby increasing the acid production amount, and improving the apparent sensitivity of a resist. Examples of such a sensitizing agent include, but not particularly limited to, benzophenones, biacetyls, pyrenes, phenothiazines, and fluorenes. These sensitizing agents can be used alone or in two or more kinds. The content of the sensitizing agent in the radiation-sensitive composition of the present embodiment, which is arbitrarily adjusted according to the kind of cyclic compound to be used, is preferably 0 to 49% by weight of the total weight of the solid component, more preferably 0 to 5% by weight, still more preferably 0 to 1% by weight, and particularly preferably 0% by weight.

(4) Surfactant

The surfactant is a component having a function of improving coatability and striation of the radiation-sensitive composition of the present embodiment, and developability of a resist or the like. Such a surfactant may be any of anionic, cationic, nonionic or amphoteric. A preferable surfactant is a nonionic surfactant. The nonionic surfactant has a good affinity with a solvent used in production of radiation-sensitive compositions and more effects. Examples of the nonionic surfactant include, but not particularly limited to, a polyoxyethylene higher alkyl ethers, polyoxyethylene higher alkyl phenyl ethers, and higher fatty acid diesters of polyethylene glycol. Examples of commercially available products include, but not particularly limited to, hereinafter by trade name, EFTOP (manufactured by Jemco Inc.), MEGAFAC (manufactured by DIC Corporation), Fluorad (manufactured by Sumitomo 3M Limited), AsahiGuard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Chemical Co., Ltd.). The content of the surfactant in the radiation-sensitive composition of the present embodiment, which is arbitrarily adjusted according to the kind of cyclic compound to be used, is preferably 0 to 49% by weight of the total weight of the solid component, more preferably 0 to 5% by weight, still more preferably 0 to 1% by weight, and particularly preferably 0% by weight.

(5) Organic Carboxylic Acid or Oxo Acid of Phosphor or Derivative Thereof

For the purpose of prevention of sensitivity deterioration or improvement of a resist pattern shape and post exposure delay stability or the like, and as an additional optional component, the radiation-sensitive composition of the present embodiment can contain an organic carboxylic acid or an oxo acid of phosphor or derivative thereof. The composition can be used in combination with the acid diffusion controlling agent, or may be used alone. As the organic carboxylic acid, for example, malonic acid, citric acid, malic acid, succinic acid, benzoic acid, and salicylic acid, or the like are preferable, but not particularly limited to these. Examples of the oxo acid of phosphor or derivative thereof include, but not particularly limited to, phosphoric acid or derivative thereof such as ester including phosphoric acid, di-n-butyl ester phosphate, and diphenyl ester phosphate; phosphonic acid or derivative thereof such as ester including phosphonic acid, dimethyl ester phosphonate, di-n-butyl ester phosphonate, phenylphosphonic acid, diphenyl ester phosphonate, and dibenzyl ester phosphonate; and phosphinic acid and derivative thereof such as ester including phosphinic acid and phenylphosphinic acid. Among them, phosphonic acid is particularly preferable.

The organic carboxylic acid or the oxo acid of phosphor or derivative thereof can be used alone or in combination of two or more kinds. The content of the organic carboxylic acid or the oxo acid of phosphor or derivative thereof in the radiation-sensitive composition of the present embodiment, which is arbitrarily adjusted according to the kind of cyclic compound to be used, is preferably 0 to 49% by weight of the total weight of the solid component, more preferably 0 to 5% by weight, still more preferably 0 to 1% by weight, and particularly preferably 0% by weight.

(6) Other Additive Agent Than the Above Dissolution Controlling Agent, Sensitizing Agent, Surfactant, and Organic Carboxylic Acid or Oxo Acid of Phosphor or Derivative Thereof Furthermore, the radiation-sensitive composition of the present embodiment can contain one kind or two kinds or more of additive agents other than the above dissolution controlling agent, sensitizing agent, and surfactant, within the range of not inhibiting the purpose of the present invention, if required. Examples of such an additive agent include, but not particularly limited to, a dye, a pigment, and an adhesion aid. For example, the radiation-sensitive composition of the present embodiment contains the dye or the pigment, and thereby a latent image of the exposed portion can be visualized and influence of halation upon exposure can be alleviated, which is preferable. The radiation-sensitive composition of the present embodiment contains the adhesion aid, and thereby adhesiveness to a substrate can be improved, which is preferable. Furthermore, examples of other additive agent include a halation preventing agent, a storage stabilizing agent, a defoaming agent, and a shape improving agent. Specific examples thereof include 4-hydroxy-4'-methylchalkone.

The total content of the above optional component (F) in the radiation-sensitive composition of the present embodiment is preferably 0 to 49% by weight of the total weight of the solid component, more preferably 0 to 5% by weight, still more preferably 0 to 1% by weight, and particularly preferably 0% by weight.

In the radiation-sensitive composition of the present embodiment, the content ratio of each component (cyclic compound/acid generating agent (C)/acid crosslinking agent (G)/acid diffusion controlling agent (E)/optional component (F)) is preferably 50 to 99.4/0.001 to 49/0.5 to 49/0.001 to 49/0 to 49, in % by weight based on the solid component, more preferably 55 to 90/1 to 40/0.5 to 40/0.01 to 10/0 to 5, still more preferably 60 to 80/3 to 30/1 to 30/0.01 to 5/0 to 1, and particularly preferably 60 to 70/10 to 25/2 to 20/0.01 to 3/0. The content ratio of each component is selected from each range so that the summation thereof is 100% by weight. In the content ratio of each component, the radiation-sensitive composition of the present embodiment has excellent performances such as sensitivity, resolution, and developability.

The radiation-sensitive composition of the present embodiment is typically prepared by dissolving each component in a solvent upon use into a homogenous solution, and then if required, filtering through a filter or the like with a pore diameter of about 0.2 μm, for example.

Examples of the solvent used in the preparation of the radiation-sensitive composition of the present embodiment include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate; propylene glycol monoalkyl ethers such as propylene glycol monomethyl ether and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbon atoms such as toluene and xylene; ketones such as 2-heptanone, 3-heptanone, 4-heptanone, cyclopentanone, and cyclohexanone; amides such as N,N-dimethylformamide, N-methylacetamide, N,N-dimethylacetamide, and N-methylpyrrolidone; and lactones such as γ-lactone. These solvents can be used alone or in combination of two or more kinds.

The radiation-sensitive composition of the present embodiment can contain a resin within the range of not inhibiting the purpose of the present invention. Examples of the resin include, but not particularly limited to, a novolac resin, polyvinyl phenols, polyacrylic acid, polyvinyl alcohol, a styrene-maleic anhydride resin, and a polymer containing acrylic acid, vinyl alcohol or vinylphenol as a monomeric unit, or derivative thereof. The content of the resin in the radiation-sensitive composition of the present embodiment, which is arbitrarily adjusted according to the kind of cyclic compound described above to be used, is preferably 30 parts by weight or less per 100 parts by weight of the above cyclic compound, more preferably 10 parts by weight or less, still more preferably 5 parts by weight or less, and particularly preferably 0 part by weight.

(Resist Pattern Formation Method)

A resist pattern formation method of the present embodiment includes the steps of forming a resist film by coating a substrate with the above radiation-sensitive composition, exposing the resist film, and developing the exposed resist film to form a resist pattern. The resist pattern of the present embodiment can also be formed as an upper layer resist in a multilayer process.

In order to form a resist pattern, a resist film is formed by coating a conventionally publically known substrate with the radiation-sensitive composition using a coating means such as spin coating, flow casting coating, and roll coating. The conventionally publically known substrate is not particularly limited. For example, a substrate for electronic components, and the one having a predetermined wiring pattern formed thereon, or the like can be exemplified. More specific examples include, but not particularly limited to, a substrate made of a metal such as a silicon wafer, copper, chromium, iron and aluminum, and a glass substrate. Examples of a wiring pattern material include, but not particularly limited to, copper, aluminum, nickel, and gold. Also if required, the substrate may be a substrate having an inorganic and/or organic film provided thereon. Examples of the inorganic film include, but not particularly limited to, an inorganic antireflection film (inorganic BARC). Examples of the organic film include, but not particularly limited to, an organic antireflection film (organic BARC). Surface treatment with hexamethylene disilazane or the like may be conducted.

Then, the coated substrate is heated if required. The heating temperatures vary according to the blending composition of the radiation-sensitive composition, or the like, but are preferably 20 to 250° C., and more preferably 20 to 150° C. By heating, the adhesiveness of a radiation-sensitive composition (resist) to a substrate may improve, which is preferable. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like are arbitrarily selected according to the compounding composition of the radiation-sensitive composition, or the like. In the resist pattern formation method of the present embodiment, in order to stably form a fine pattern with a high degree of accuracy in exposure, the resist film is preferably heated after radiation irradiation. The heating temperatures vary according to the compounding composition of the radiation-sensitive composition, or the like, but are preferably 20 to 250° C., and more preferably 20 to 150° C.

Next, by developing the exposed resist film in a developing solution (development step), a predetermined resist pattern is formed. The developing solution is a solvent having a solubility parameter (SP value) close to that of the cyclic compound described above to be used is preferably selected. For example, a polar solvent such as a ketone-based solvent, an ester-based solvent, an alcohol-based solvent, an amide-based solvent, and an ether-based solvent; and a hydrocarbon-based solvent, or an alkaline aqueous solution can be used.

Examples of the ketone-based solvent include, but not particularly limited to, 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

Examples of the ester-based solvent include, but not particularly limited to, methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

Examples of the alcohol-based solvent include, but not particularly limited to, an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include, but not particularly limited to, dioxane and tetrahydrofuran in addition to the above glycol ether-based solvents.

Examples of the amide-based solvent which can be used include, but not particularly limited to, N-methyl-2-pyrrolidone, N,N-dimethylacetamide, N,N-dimethylformamide, phosphoric hexamethyltriamide, and 1,3-dimethyl-2-imidazolidinone.

Examples of the hydrocarbon-based solvent include, but not particularly limited to, an aromatic hydrocarbon-based solvent such as toluene and xylene; and an aliphatic hydrocarbon-based solvent such as pentane, hexane, octane, and decane.

A plurality of these solvents may be mixed, or the solvent may be used by mixing the solvent with a solvent other than those described above or water within the range having performance. However, in order to sufficiently exhibit the effect of the present invention, the water content ratio based on the whole developing solution is less than 70% by mass, preferably less than 50% by mass, more preferably less than 30% by mass, and still more preferably less than 10% by mass. Particularly preferably, the developing solution is substantially moisture free. That is, the content of the organic solvent in the developing solution is 30% by mass or more and 100% by mass or less based on the total amount of the developing solution, preferably 50% by mass or more and 100% by mass or less, more preferably 70% by mass or more and 100% by mass or less, still more preferably 90% by mass or more and 100% by mass or less, and particularly preferably 95% by mass or more and 100% by mass or less.

Examples of the alkaline aqueous solution include, but not particularly limited to, an alkaline compound such as mono-, di- or tri-alkylamines, mono-, di- or tri-alkanolamines, heterocyclic amines, tetramethyl ammonium hydroxide (TMAH), and choline.

Particularly, the developing solution containing at least one kind of solvent selected from a ketone-based solvent, an ester-based solvent, an alcohol-based solvent, an amide-based solvent, and an ether-based solvent improves resist performance such as resolution and roughness of the resist pattern, which is preferable.

The vapor pressure of the developing solution is preferably 5 kPa or less at 20° C., more preferably 3 kPa or less, and particularly preferably 2 kPa or less. The evaporation of the developing solution on the substrate or in a developing cup is inhibited by setting the vapor pressure of the developing solution to 5 kPa or less, to improve temperature uniformity within a wafer surface, thereby resulting in improvement in size uniformity within the wafer surface.

Specific examples of the solvent for the developing solution having a vapor pressure of 5 kPa or less at 20° C. include, but not particularly limited to, a ketone-based solvent such as 1-octanone, 2-octanone, 1-nonanone, 2-nonanone, 4-heptanone, 2-hexanone, diisobutyl ketone, cyclohexanone, methylcyclohexanone, phenylacetone, and methyl isobutyl ketone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate, and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monoethyl ether, triethylene glycol monoethyl ether, and methoxymethyl butanol; an ether-based solvent such as tetrahydrofuran; an amide-based solvent such as N-methyl-2-pyrrolidone, N,N-dimethylacetamide, and N,N-dimethylformamide; an aromatic hydrocarbon-based solvent such as toluene and xylene; and an aliphatic hydrocarbon-based solvent such as octane and decane.

Specific examples of the developing solution having a vapor pressure of 2 kPa or less which is a particularly preferable range include, but not particularly limited to, a ketone-based solvent such as 1-octanone, 2-octanone, 1-nonanone, 2-nonanone, 4-heptanone, 2-hexanone, diisobutyl ketone, cyclohexanone, methylcyclohexanone, and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate, and propyl lactate; an alcohol-based solvent such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an amide-based solvent such as N-methyl-2-pyrrolidone, N,N-dimethylacetamide, and N,N-dimethylformamide; an aromatic hydrocarbon-based solvent such as xylene; and an aliphatic hydrocarbon-based solvent such as octane and decane.

To the developing solution, a surfactant can be added in an appropriate amount, if required.

The surfactant is not particularly limited but, for example, an ionic or nonionic fluorine-based and/or silicon-based surfactant can be used. Examples of the fluorine-based and/or silicon-based surfactant include the surfactants described in Japanese Patent Application Laid-Open Nos. 62-36663, 61-226746, 61-226745, 62-170950, 63-34540, 7-230165, 8-62834, 9-54432, and 9-5988, and U.S. Pat. Nos. 5,405,720, 5,360,692, 5,529,881, 5,296,330, 5,436,098, 5,576,143, 5,294,511, and 5,824,451. The surfactant is preferably a nonionic surfactant. The nonionic surfactant is not particularly limited, but a fluorine-based surfactant or a silicon-based surfactant is more preferably used, for example.

The amount of the surfactant used is usually 0.001 to 5% by mass based on the total amount of the developing solution, preferably 0.005 to 2% by mass, and more preferably 0.01 to 0.5% by mass.

The development method is not particularly limited. For example, a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method), or the like may be applied. The time for conducting the pattern development is not particularly limited, but is preferably 10 seconds to 90 seconds.

After the step of conducting development, a step of stopping the development by the replacement with another solvent may be practiced in the resist pattern formation method of the present embodiment.

Furthermore, the resist pattern formation method of the present embodiment preferably includes a step (rinsing step) of rinsing the resist film with a rinsing solution containing an organic solvent after the development step.

The rinsing solution used in the rinsing step after development step is not particularly limited as long as the rinsing solution does not dissolve the resist pattern cured by crosslinking. A solution containing a general organic solvent or water may be used as the rinsing solution. As the rinsing solution, a rinsing solution containing at least one kind of organic solvent selected from a hydrocarbon-based solvent, a ketone-based solvent, an ester-based solvent, an alcohol-based solvent, an amide-based solvent, and an ether-based solvent is preferably used, but not particularly limited to these. More preferably, after development step, a step of rinsing the film by using a rinsing solution containing at least one kind of organic solvent selected from the group consisting of a ketone-based solvent, an ester-based solvent, an alcohol-based solvent and an amide-based solvent is conducted. Still more preferably, after development step, a step of rinsing the film by using a rinsing solution containing an alcohol-based solvent or an ester-based solvent is conducted. Yet still more preferably, after development step, a step of rinsing the film by using a rinsing solution containing a monohydric alcohol is conducted. Particularly preferably, after development step, a step of rinsing the film by using a rinsing solution containing a monohydric alcohol having 5 or more carbon atoms is conducted. The time for rinsing the pattern is not particularly limited, but is preferably 10 seconds to 90 seconds.

Herein, examples of the monohydric alcohol used in the rinsing step after development step include, but not particularly limited to, a linear, branched or cyclic monohydric alcohol. Specifically, 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol or the like can be used. As the particularly preferable monohydric alcohol having 5 or more carbon atoms, 1-hexanol, 2-hexanol, 4-methyl-2-pentanol, 1-pentanol, and 3-methyl-1-butanol or the like can be used, but not particularly limited to these.

A plurality of these components may be mixed, or the component may be used by mixing the component with an organic solvent other than those described above.

The water content ratio in the rinsing solution is preferably 10% by mass or less, more preferably 5% by mass or less, and particularly preferably 3% by mass or less. By setting the water content ratio in the rinsing solution to 10% by mass or less, better development characteristics can be obtained.

The vapor pressure at 20° C. of the rinsing solution used after development step is preferably 0.05 kPa or more and 5 kPa or less, more preferably 0.1 kPa or more and 5 kPa or less, and further preferably 0.12 kPa or more and 3 kPa or less. By setting the vapor pressure of the rinsing solution to 0.05 kPa or more and 5 kPa or less, the temperature uniformity in the wafer surface is enhanced and moreover, swelling due to permeation of the rinsing solution is further inhibited. As a result, the dimensional uniformity in the wafer surface is further improved.

The rinsing solution may also be used after adding an appropriate amount of a surfactant to the rinsing solution.

In the rinsing step, the wafer after development step is preferably rinsed using the organic solvent-containing rinsing solution. The method for rinsing treatment is not particularly limited. However, for example, a method for continuously ejecting a rinsing solution on a substrate spinning at a constant speed (spin coating method), a method for dipping a substrate in a bath filled with a rinsing solution for a fixed time (dipping method), and a method for spraying a rinsing solution on a substrate surface (spraying method), or the like can be applied. Above all, it is preferable to conduct the rinsing treatment by the spin coating method and after the rinsing, spin the substrate at a rotational speed of 2,000 rpm to 4,000 rpm, to remove the rinsing solution from the substrate surface.

After forming the resist pattern, a pattern wiring substrate is obtained by etching. Etching can be conducted by a publicly known method such as dry etching using plasma gas, and wet etching with an alkaline solution, a cupric chloride solution, and a ferric chloride solution or the like.

After forming the resist pattern, plating can also be conducted. Examples of the above plating method include, but not particularly limited to, copper plating, solder plating, nickel plating, and gold plating.

The remaining resist pattern after etching can be peeled by an organic solvent. Examples of the above organic solvent include, but not particularly limited to, PGMEA (propylene glycol monomethyl ether acetate), PGME (propylene glycol monomethyl ether), and EL (ethyl lactate). Examples of the above peeling method include, but not particularly limited to, a dipping method and a spraying method. A wiring substrate having a resist pattern formed thereon may be a multilayer wiring substrate, and may have a small diameter through hole.

In the present embodiment, the wiring substrate can also be formed by a method for forming a resist pattern, then depositing a metal in vacuum, and subsequently dissolving the resist pattern in a solution, i.e., a liftoff method.

EXAMPLES

Embodiments of the present invention will be more specifically described with reference to examples below. However, the present invention is not limited to these examples. In the following syntheses and synthesis examples, the structure of each compound was confirmed by $^1$H-NMR measurement.

(Synthesis 1) Synthesis of CR-1A (Cyclic Compound (A))

Under a nitrogen gas stream, resorcinol manufactured by Kanto Chemical Co., Inc. (22 g, 0.2 mol), 4-isopropylbenzaldehyde (29.6 g, 0.2 mol), and dehydrated ethanol (200 mL) were charged to a four necked flask (1000 mL) sufficiently dried, substituted with nitrogen, and equipped with a dropping funnel, a Dimroth condenser tube, a thermometer, and a stirring blade, to prepare an ethanol solution. The ethanol solution was heated to 85° C. by a mantle heater while stirring. Then, 75 mL of concentrated hydrochloric acid (35%) was dropped in the ethanol solution through the dropping funnel for 30 minutes, and then continuously stirred at 85° C. for 3 hours for reaction. After the reaction terminated, the obtained reaction liquid was stood to cool, and after it reached room temperature, it was cooled in an ice bath. The reaction liquid was left at rest for 1 hour, to produce a light yellow crude crystal. The produced light yellow crude crystal was filtered, to obtain a crude crystal. The obtained crude crystal was washed twice with 500 mL methanol, filtered, and dried in a vacuum to obtain 45.6 g of a compound. The result of LC-MS analysis showed that the compound had a molecular weight of 960 which was the same as that of an objective compound represented by the following formula (CR-1A). The chemical shift value (δ ppm, TMS standard) of the obtained compound measured by $^1$H-NMR in a deuterated dimethyl sulfoxide solvent was 1.1 to 1.2 (m, 24H), 2.6 to 2.7 (m, 4H), 5.5 (s, 4H), 6.0 to 6.8 (m, 24H), and 8.4 to 8.5 (d, 8H). From these results, the obtained compound was identified as an objective compound (hereinafter, described also as "CR-1A") represented by the following formula (CR-1A) (yield: 95%).

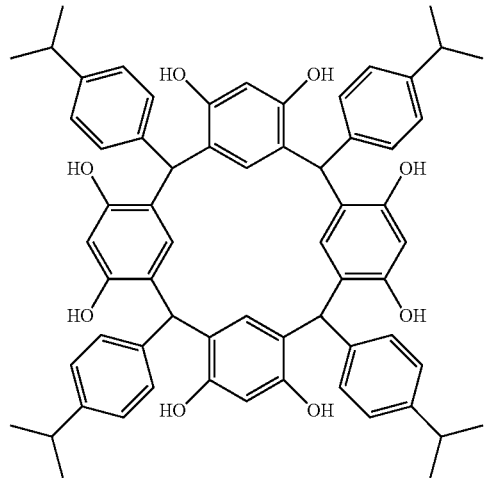

(CR-1A)

(Synthesis 2) Synthesis of CR-2A (Cyclic Compound (A))

In the same manner as in synthesis 1 except for using 4-cyclohexylbenzaldehyde (46.0 g, 0.2 mol) in place of 4-isopropylbenzaldehyde, 50 g of a compound was obtained. The result of LC-MS analysis showed that the obtained compound had a molecular weight of 1121 which was the same as that of an objective compound represented by the following formula (CR-2A). The chemical shift value (δ ppm, TMS standard) of the obtained compound measured by $^1$H-NMR in a deuterated dimethyl sulfoxide solvent was 0.8 to 1.9 (m, 44H), 5.5 to 5.6 (d, 4H), 6.0 to 6.8 (m, 24H), and 8.4 to 8.5 (m, 8H). From these results, the obtained compound was identified as an objective compound (hereinafter, described also as "CR-2A") represented by the following formula (CR-2A) (yield: 91%).

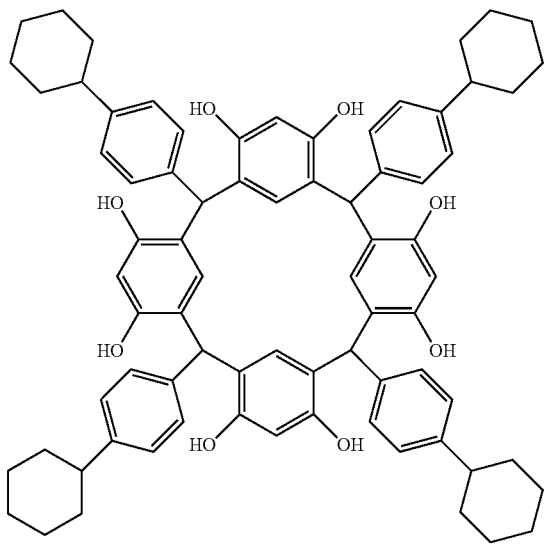

(CR-2A)

Synthesis Example 1

Synthesis of CR-1 (Cyclic Compound)

In a four necked flask (1000 mL) sufficiently dried, substituted with nitrogen, and equipped with a dropping funnel, a Dimroth condenser tube, a thermometer, and a stirring blade, 3.6 g (40 mmol) of acryloyl chloride was dropped to a solution of 9.6 g (10 mmol) of CR-1A synthesized in synthesis 1 and 4 g (40 mmol) of triethylamine in 300 mL of THF cooled in an ice bath under a nitrogen gas stream. The resultant solution was stirred at room temperature for 1 hour for reaction. After the reaction terminated, the obtained reaction liquid was added to 1000 ml of cold water, and the deposited solid was filtered. The obtained solid was purified by column chromatography, to obtain 10.6 g of a compound.

The chemical shift value (δ ppm, TMS standard) of the obtained compound measured by $^1$H-NMR in a deuterated dimethyl sulfoxide solvent was 1.1 to 1.2 (m, 24H), 2.6 to 2.7 (m, 4H), 5.5 (m, 4H), 5.7 (m, 4H), 6.0 to 6.8 (m, 32H), and 8.4 to 8.5 (m, 4H). From these results, the obtained compound was identified as a compound (hereinafter, described also as "CR-1") in which 50 mol % of hydrogen atoms of phenolic hydroxyl groups in CR-1A were substituted with acryloyl groups, and which was represented by the following formula (CR-1).

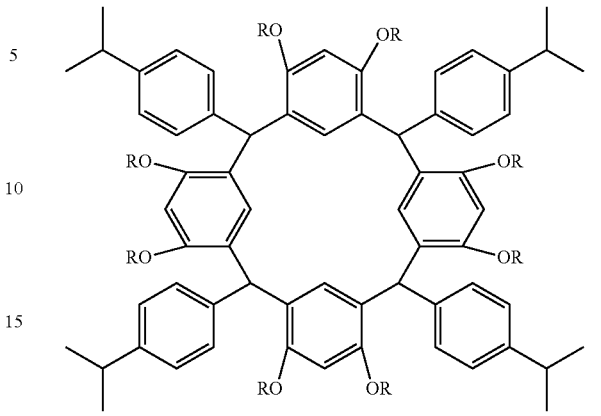

(CR-1)

(In CR-1, 50 mol % of R were acryloyl groups, and the remainder 50 mol % were hydrogen atoms.)

Synthesis Example 2

Synthesis of CR-2 (Cyclic Compound)

In the same manner as in synthesis example 1 except for using CR-2A (11.2 g, 10 mmol) in place of CR-1A, 11.2 g of a compound was obtained. The chemical shift value (δ ppm, TMS standard) of the obtained compound measured by $^1$H-NMR in a deuterated dimethyl sulfoxide solvent was 0.8 to 1.9 (m, 44H), 5.5 to 5.6 (d, 4H), 5.7 (s, 4H), 6.0 to 6.8 (m, 32H), and 8.4 to 8.5 (m, 4H). From these results, the obtained compound was identified as a compound (hereinafter, described also as "CR-2") in which 50 mol % of hydrogen atoms of phenolic hydroxyl groups in CR-2A were substituted with acryloyl groups, and which was represented by the following formula (CR-2).

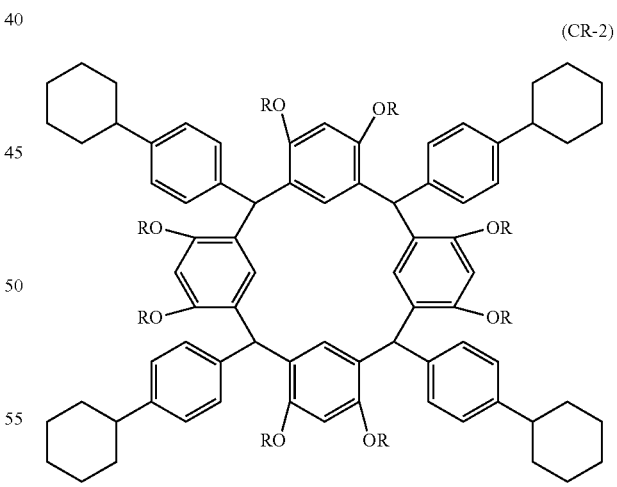

(CR-2)

(In CR-2, 50 mol % of R were acryloyl groups, and the remainder 50 mol % were hydrogen atoms.)

Synthesis Example 3

Synthesis of CR-3 (Cyclic Compound)

In the same manner as in synthesis example 1 except for using 10.8 g (120 mmol) of acryloyl chloride in place of 3.6 g (40 mmol) of acryloyl chloride, 11.0 g of a compound was obtained. The result of LC-MS analysis showed that the obtained compound had a molecular weight of 1393 which was the same as that of an objective compound represented by the following formula (CR-3). The chemical shift value (δ ppm, TMS standard) of the obtained compound measured by $^1$H-NMR in a deuterated dimethyl sulfoxide solvent was 1.1 to 1.2 (m, 24H), 2.6 to 2.7 (m, 4H), 5.5 (s, 4H), 5.7 (s, 8H), and 6.0 to 6.8 (m, 40H). From these results, the obtained compound was identified as a compound (hereinafter, described also as "CR-3") in which 100 mol % of the hydrogen atoms of the phenolic hydroxyl groups in CR-1A were substituted with acryloyl groups, and which was represented by the following formula (CR-3).

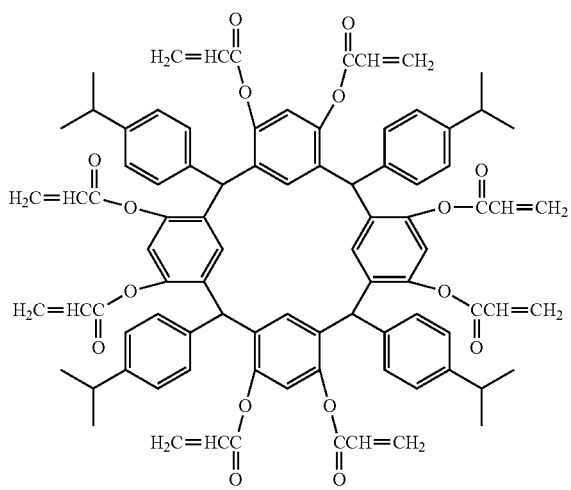

(CR-3)

Synthesis Example 4

Synthesis of CR-4 (Cyclic Compound)

In the same manner as in synthesis example 2 except for using 10.8 g (120 mmol) of acryloyl chloride in place of 3.6 g (40 mmol) of acryloyl chloride, 11.4 g of a compound was obtained. The result of LC-MS analysis showed that the obtained compound had a molecular weight of 1553 which was the same as that of an objective compound represented by the following formula (CR-4). The chemical shift value (δ ppm, TMS standard) of the obtained compound measured by $^1$H-NMR in a deuterated dimethyl sulfoxide solvent was 0.8 to 1.9 (m, 44H), 5.5 to 5.6 (d, 4H), 5.7 (s, 8H), and 6.0 to 6.8 (m, 40H). From these results, the obtained compound was identified as a compound (hereinafter, described also as "CR-4") in which 100 mol % of hydrogen atoms of phenolic hydroxyl groups in CR-2A were substituted with acryloyl groups, and which was represented by the following formula (CR-4).

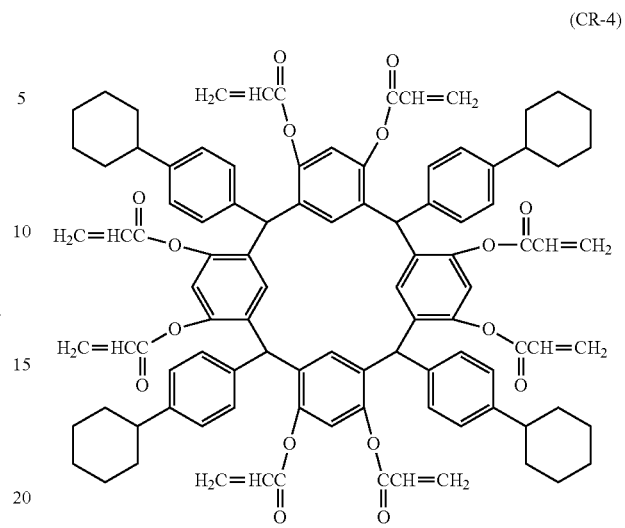

(CR-4)

Synthesis Example 5

Synthesis of CR-5 (Cyclic Compound)

In the same manner as in synthesis example 3 except for using 12.48 g (120 mmol) of methacryloyl chloride in place of 10.8 g (120 mmol) of acryloyl chloride, 11.0 g of a compound was obtained. The result of LC-MS analysis showed that the obtained compound had a molecular weight of 1521 which was the same as that of an objective compound represented by the following formula (CR-5). The chemical shift value (δ ppm, TMS standard) of the obtained compound measured by $^1$H-NMR in a deuterated dimethyl sulfoxide solvent was 1.1 to 1.2 (m, 24H), 1.9 (s, 12H), 2.6 to 2.7 (m, 4H), 5.5 (s, 4H), 5.7 (s, 8H), and 6.0 to 6.8 (m, 32H). From these results, the obtained compound was identified as a compound (hereinafter, described also as "CR-5") in which 100 mol % of hydrogen atoms of phenolic hydroxyl groups in CR-1A were substituted with methacryloyl groups, and which was represented by the following formula (CR-5).

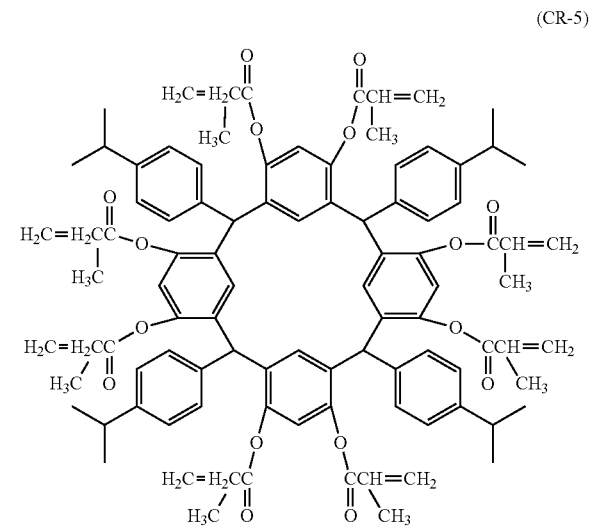

(CR-5)

Synthesis Example 6

Synthesis of CR-6 (Cyclic Compound)

In the same manner as in synthesis example 4 except for using 12.48 g (120 mmol) of methacryloyl chloride in place of 10.8 g (120 mmol) of acryloyl chloride, 11.0 g of a compound was obtained. The result of LC-MS analysis showed that the obtained compound had a molecular weight of 1681 which was the same as that of an objective compound represented by the following formula (CR-6). The chemical shift value (δ ppm, TMS standard) of the obtained compound measured by $^1$H-NMR in a deuterated dimethyl sulfoxide solvent was 0.8 to 1.9 (m, 44H), 2.0 (s, 24H), 5.5 to 5.6 (d, 4H), 5.7 (s, 8H), and 6.0 to 6.8 (m, 32H). From these results, the obtained compound was identified as a compound (hereinafter, described also as "CR-6") in which 100 mol % of hydrogen atoms of phenolic hydroxyl groups in CR-2A were substituted with methacryloyl groups, and which was represented by the following formula (CR-6).

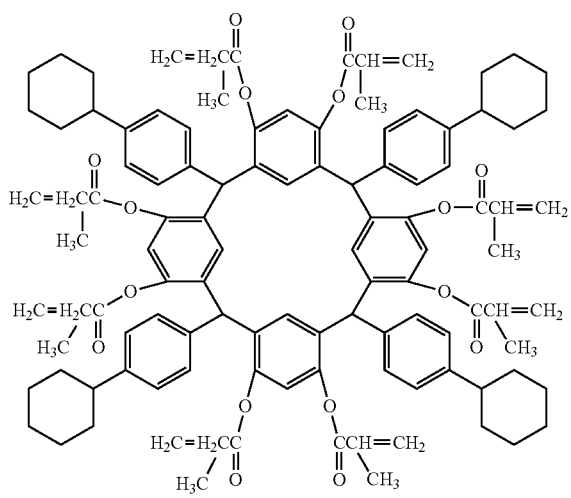

(CR-6)

Examples 1 to 6 and Comparative Examples 1 to 2

Solubility Test of Compound in Safe Solvent

The dissolution amounts of compounds obtained in the above synthesis examples 1 to 6 and syntheses 1 and 2 in propylene glycol monomethyl ether (PGME) and cyclohexanone (CHN) were evaluated as follows. The evaluation result is shown in Table 1.

[Evaluation Criterion]
A: 5.0% by mass≤dissolution amount
B: 3.0% by mass≤dissolution amount<5.0% by mass
C: dissolution amount<3.0% by mass
*dissolution amount (% by mass)=mass (g) of compound dissolved in 100 g of solvent of 23° C./(100 g of mass of solvent+mass (g) of compound dissolved in 100 g of solvent of 23° C.)×100

TABLE 1

|  | Cyclic compound | PGME | CHN |
| --- | --- | --- | --- |
| Example 1 | CR-1 | A | B |
| Example 2 | CR-2 | A | A |
| Example 3 | CR-3 | B | A |
| Example 4 | CR-4 | B | A |
| Example 5 | CR-5 | B | A |
| Example 6 | CR-6 | B | A |
| Comparative Example 1 | CR-1A | B | C |
| Comparative Example 2 | CR-2A | B | B |

From the results of the solubility test of the compounds in the safe solvent, it was found that examples 1 to 6 using the compounds of CR-1 to 6 show better results of larger dissolution amounts in PGME and CHN, as compared to comparative examples 1 and 2 using CR-1A and CR-2A.

Examples 7 and 8 and Comparative Examples 3 and 4

(1) Preparation of Radiation-Sensitive Compositions

Components described in Table 2 were blended into homogeneous solutions, and then filtered through a membrane filter made of Teflon with a pore diameter of 0.1 μm to prepare radiation-sensitive compositions.

TABLE 2

|  | Compound (g) | Acid generating agent (C) (g) | Acid crosslinking agent (G) (g) | Acid diffusion controlling agent (E) (g) | Solvent (g) |
| --- | --- | --- | --- | --- | --- |
| Example 7 | CR-3 1.0 | P-1 0.3 | C-1 0.3 | Q-1 0.03 | S-1 30.0 |
| Example 8 | CR-4 1.0 | P-1 0.3 | C-1 0.3 | Q-1 0.03 | S-1 30.0 |
| Comparative Example 3 | CR-1A 1.0 | P-1 0.3 | C-1 0.3 | Q-1 0.03 | S-1 30.0 |
| Comparative Example 4 | CR-2A 1.0 | P-1 0.3 | C-1 0.3 | Q-1 0.03 | S-1 30.0 |

Acid Generating Agent (C)
P-1: triphenylbenzenesulfonium trifluoromethanesulfonate (Midori Kagaku Co., Ltd.)
Acid Crosslinking Agent (G)
C-1: NIKALAC MW-100LM (Sanwa Chemical Co., Ltd.)
Acid Diffusion Controlling Agent (E)
Q-1: trioctylamine (Tokyo Kasei Kogyo Co., Ltd.) Solvent
S-1: propylene glycol monomethyl ether (Tokyo Kasei Kogyo Co., Ltd.)

(2) Patterning Test

Patterning test was conducted as follows by using the radiation-sensitive composition prepared above.

A clean silicon wafer was spin coated with the radiation-sensitive composition prepared above, and then prebaked (PB) before exposure in an oven of 110° C. to form a resist film with a thickness of 60 nm. The resist film was irradiated with electron beams of 1:1 line and space setting with a 50 nm interval, a 40 nm interval, and a 30 nm interval using an electron beam lithography system (ELS-7500 manufactured by ELIONIX INC.). After irradiation, the resist films were heated at 110° C. for 90 seconds. The resist films formed from the radiation-sensitive compositions prepared in examples 7 and 8 were immersed in a propylene glycol-monomethyl ether acetate developing solution for 30 seconds for development. The resist films formed from the radiation-sensitive compositions prepared in comparative examples 3 and 4 were immersed in a 2.38% by mass TMAH aqueous solution for development. Subsequently, the resist films were washed with ultrapure water for 30 seconds, and dried to form negative type resist patterns.

The obtained resist patterns were observed by a scanning electron microscope (S-4800 manufactured by Hitachi High-Technologies Corporation). The minimum line width of the pattern which could be formed was used as the resolution of the pattern. The rectangular pattern shape was evaluated as goodness. For line edge roughness, the irregularity of the pattern of less than 5 nm was evaluated as goodness. A dose amount ($\mu C/cm^2$) in this case was used as sensitivity. The dose amount of less than 150 $\mu C/cm^2$ was evaluated as goodness.

The result of the patterning test showed that, in the radiation-sensitive compositions of examples 7 and 8, a resist pattern with good resolution of 30 nm and high sensitivity could be obtained. The result of the patterning test showed that the roughness of the pattern was also small, and the shape was also good.

On the other hand, in the radiation-sensitive compositions of comparative examples 3 and 4, a resist pattern with good resolution of 40 nm could be obtained, but, a resist pattern with good resolution of 30 nm could not be obtained.

As described above, the composition containing the compound (for example, CR-3 and CR-4) of the present embodiment was found to have higher sensitivity, and enable the formation of the resist pattern having a better shape having smaller roughness than that of the composition containing the corresponding comparative compound (for example, CR-1A and CR-2A). As long as the requirements of the above present embodiment are met, compounds other than those described in examples also exhibit the same effects.

INDUSTRIAL APPLICABILITY

The present invention is preferably used in a cyclic compound represented by a specific chemical constitution formula, which is useful as an acid amplification type non-polymeric resist material, a radiation-sensitive composition containing the same, and a resist pattern formation method using the radiation-sensitive composition.

The invention claimed is:

1. A cyclic compound having a molecular weight of 500 to 5000 and represented by formula (4):

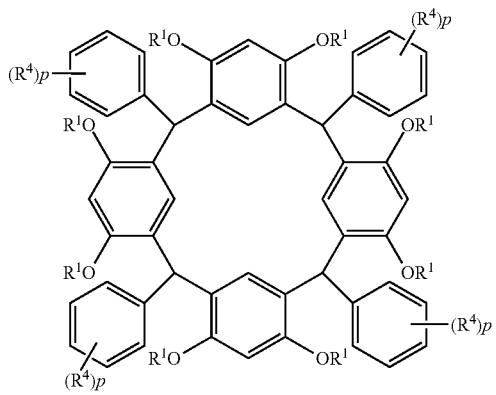

wherein
R$^1$ are each independently a hydrogen atom, a cyano group, a nitre group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted alkylsilyl group having 1 to 20 carbon atoms, or a substituted or non-substituted alkenyl group having 2 to 20 carbon atoms;

R$^4$ are each independently a cyano group, a nitre group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted alkoxy group having 1 to 20 carbon atoms, or a substituted or non-substituted alkylsilyl group having 1 to 20 carbon atoms;

p is an integer of 0 to 5; and at least one of R$^1$ is a (meth)acryloyl group.

2. The cyclic compound according to claim 1, wherein the cyclic compound represented by the formula (4) is represented by the formula (5):

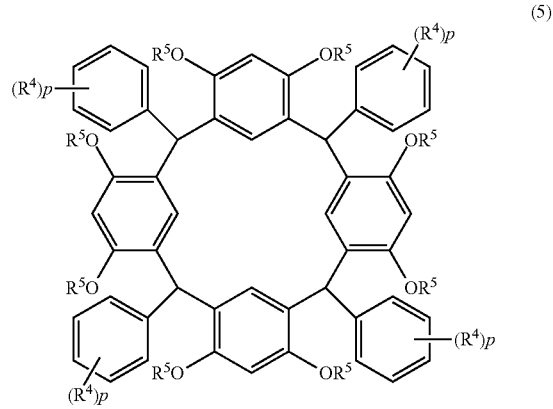

wherein
R$^4$ are each independently a cyano group, a nitre group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted alkoxy group having 1 to 20 carbon atoms, or a substituted or non-substituted alkylsilyl group having 1 to 20 carbon atoms;

p is an integer of 0 to 5; and

R$^5$ is a (meth)acryloyl group.

3. A method for producing the cyclic compound according to any one of claims 1 or 2, comprising the steps of:
a condensation reaction of one or more aldehyde compounds (A1) with one or more phenolic compounds (A2) to obtain a cyclic compound (A); and
a dehydrohalogenation reaction of the cyclic compound (A) with one or more (meth)acryloyl halides.

4. The method for producing the cyclic compound according to claim 3, wherein:

the aldehyde compound (A1) has 1 to 4 formyl groups and has 1 to 59 carbon atoms; and the phenolic compound (A2) has 1 to 3 phenolic hydroxyl groups and has 6 to 15 carbon atoms.

5. A radiation-sensitive composition comprising a solid component containing the cyclic compound according to claim 1 and a solvent.

6. The radiation-sensitive composition according to claim 5, comprising 1 to 80% by weight of the solid component.

7. The radiation-sensitive composition according to claim 5, wherein a content of the cyclic compound is 50 to 99.999% by weight based on a total weight of the solid component.

8. The radiation-sensitive composition according to claim 5, further comprising an acid generating agent (C) which directly or indirectly generates acid upon exposure to any radiation selected from the group consisting of visible light, ultraviolet, excimer laser, electron beam, extreme ultraviolet (EUV), X-ray, and ion beam.

9. The radiation-sensitive composition according to claim 5, further comprising an acid crosslinking agent (G).

10. The radiation-sensitive composition according to claim 5, further comprising an acid diffusion controlling agent (E).

11. The radiation-sensitive composition according to claim 5, wherein the solid component comprises 50 to 99.4% by weight of the cyclic compound, 0.001 to 49% by weight of an acid generating agent (C), 0.5 to 49% by weight of an acid crosslinking agent (G), and 0.001 to 49% by weight of an acid diffusion controlling agent (E).

12. The radiation-sensitive composition according to claim 5, forming an amorphous film by spin coating.

13. The radiation-sensitive composition according to claim 12, wherein a dissolution rate of the amorphous film into a developing solution at 23° C. is 10 angstrom/sec or more.

14. The radiation-sensitive composition according to claim 12, wherein a dissolution rate of the amorphous film into a developing solution is 5 angstrom/sec or less after exposed to KrF excimer laser, extreme ultraviolet, electron beam, or X-ray, or after heated at 20 to 250° C.

15. A method for forming a resist pattern, comprising the steps of:

forming a resist film by coating a substrate with the radiation-sensitive composition according to claim 5;
exposing the resist film; and
developing the exposed resist film.

* * * * *